United States Patent
Kleckner et al.

(10) Patent No.: US 11,759,647 B2
(45) Date of Patent: *Sep. 19, 2023

(54) MEDICAL DEVICE AND METHOD FOR POWER REDUCTION FOR ARRHYTHMIA DETECTION

(71) Applicant: Medtronic, Inc., Minneapolis, MN (US)

(72) Inventors: Karen J. Kleckner, Blaine, MN (US); Wade M. Demmer, Coon Rapids, MN (US); Vincent P. Ganion, Blaine, MN (US); Yanina Grinberg, Plymouth, MN (US); Paul R. Solheim, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/408,390

(22) Filed: Aug. 21, 2021

(65) Prior Publication Data
US 2021/0379390 A1    Dec. 9, 2021

Related U.S. Application Data

(63) Continuation of application No. 16/283,087, filed on Feb. 22, 2019, now Pat. No. 11,097,117.

(51) Int. Cl.
*A61N 1/378* (2006.01)
*A61N 1/05* (2006.01)
(Continued)

(52) U.S. Cl.
CPC .......... *A61N 1/378* (2013.01); *A61N 1/059* (2013.01); *A61N 1/3624* (2013.01);
(Continued)

(58) Field of Classification Search
CPC ............... A61N 1/378; A61N 1/059
(Continued)

(56) References Cited

U.S. PATENT DOCUMENTS

| 4,708,144 A | 11/1987 | Hamilton et al. |
| 4,880,004 A | 11/1989 | Baker et al. |

(Continued)

FOREIGN PATENT DOCUMENTS

WO    20120057862 A1    5/2012

OTHER PUBLICATIONS

PCT International Search Repod dated Jun. 30, 2020, corresponding to counterpart PCT Application No. PCT/US2020/018991; 3 pages.
(Continued)

*Primary Examiner* — Catherine M Voorhees
*Assistant Examiner* — Roland Dinga

(57) ABSTRACT

A medical device and method conserve electrical power used in monitoring cardiac arrhythmias. The device includes a sensing circuit configured to sense a cardiac signal, a power source and a control circuit having a processor powered by the power source. The control circuit is configured to operate in a normal state by waking up the processor to analyze the cardiac electrical signal for determining a state of an arrhythmia. The control circuit switches from the normal state to a power saving state that includes waking up the processor at a lower rate than during the normal state.

22 Claims, 8 Drawing Sheets

(51) Int. Cl.
    *A61N 1/362*      (2006.01)
    *A61N 1/365*      (2006.01)
    *A61N 1/39*      (2006.01)
    *A61B 5/352*      (2021.01)
    *A61B 5/361*      (2021.01)
    *A61B 5/363*      (2021.01)

(52) U.S. Cl.
    CPC ..... *A61N 1/36542* (2013.01); *A61N 1/36592* (2013.01); *A61N 1/3956* (2013.01); *A61N 1/3975* (2013.01); *A61B 5/352* (2021.01); *A61B 5/361* (2021.01); *A61B 5/363* (2021.01); *A61B 2560/0209* (2013.01)

(58) Field of Classification Search
    USPC .......................................................... 607/7
    See application file for complete search history.

(56) References Cited

U.S. PATENT DOCUMENTS

| | | |
|---|---|---|
| 4,903,699 A | 2/1990 | Baker et al. |
| 5,103,819 A | 4/1992 | Baker et al. |
| 5,507,782 A | 4/1996 | Kieval et al. |
| 5,800,466 A | 9/1998 | Routh et al. |
| 6,016,448 A | 1/2000 | Busacker et al. |
| 6,112,119 A | 8/2000 | Schuelke et al. |
| 6,185,454 B1 | 2/2001 | Thompson |
| 6,185,460 B1 | 2/2001 | Thompson |
| 6,418,343 B1 | 7/2002 | Zhang et al. |
| 6,453,198 B1 | 9/2002 | Torgerson et al. |
| 6,584,350 B2 | 6/2003 | Kim et al. |
| 6,862,476 B2 | 3/2005 | Mouchawar et al. |
| 7,245,965 B1 | 7/2007 | Pei et al. |
| 7,463,926 B1 | 12/2008 | Levine et al. |
| 7,623,911 B2 | 11/2009 | Sarkar et al. |
| 7,668,593 B1 | 2/2010 | Pei et al. |
| 7,923,922 B2 | 4/2011 | Geohegan et al. |
| 8,099,164 B2 | 1/2012 | Gillberg et al. |
| 8,195,291 B2 | 6/2012 | Norton et al. |
| 8,532,785 B1 | 9/2013 | Crutchfield et al. |
| 9,242,109 B2 | 1/2016 | Gordon et al. |
| 9,486,155 B2 | 11/2016 | Sarkar et al. |
| 10,045,710 B2 | 8/2018 | Higgins et al. |
| 2016/0051823 A1 | 2/2016 | Maile et al. |

OTHER PUBLICATIONS

PCT International Preliminary Report on Patentability dated Aug. 10, 2021, corresponding to counterpart PCT Application No. PCT/US2020/018991; 6 pages.

MEDICAL DEVICE AND METHOD FOR POWER REDUCTION FOR ARRHYTHMIA DETECTION

REFERENCE TO RELATED APPLICATIONS

This application is a continuation of U.S. patent application Ser. No. 16/283,087, filed on Feb. 22, 2019, incorporated herein by reference in its entirety.

TECHNICAL FIELD

The disclosure relates generally to medical devices and, in particular, to a device and method for detecting cardiac arrhythmias with reduced power requirements during a power saving state.

BACKGROUND

A variety of medical devices for monitoring a physiological condition of a patient and/or delivering a therapy have been clinically implanted or proposed for clinical implantation in patients and/or have been incorporated into a wearable medical device. Some implantable medical devices (IMDs), for example, may employ one or more elongated electrical leads carrying stimulation electrodes, sense electrodes, and/or other sensors. IMDs may deliver therapy to or monitor conditions of a variety of organs, nerves, muscle or tissue, such as the heart, brain, stomach, spinal cord, pelvic floor, or the like. Implantable medical leads may be configured to position electrodes or other sensors at desired locations for delivery of electrical stimulation or sensing of physiological conditions. For example, electrodes or sensors may be carried along a distal portion of a lead that is extended subcutaneously, transvenously, or submuscularly. A proximal portion of the lead may be coupled to an implantable medical device housing, which contains circuitry such as signal generation circuitry and/or sensing circuitry.

Some IMDs, such as cardiac pacemakers or implantable cardioverter defibrillators (ICDs), provide therapeutic electrical stimulation to the heart of the patient via electrodes carried by one or more implantable leads and/or the housing of the pacemaker or ICD. The leads may be transvenous, e.g., advanced into the heart through one or more veins to position endocardial electrodes in intimate contact with the heart tissue. Other leads may be non-transvenous leads implanted outside the heart, e.g., implanted epicardially, pericardially, or subcutaneously. The electrodes are used to sense intrinsic cardiac electrical signals for monitoring the heart rhythm and deliver electrical stimulation pulses to the heart to address abnormal cardiac rhythms.

IMDs capable of delivering electrical stimulation for treating abnormal cardiac rhythms typically sense signals representative of intrinsic depolarizations of the heart and analyze the sensed signals to identify the abnormal rhythms. Upon detection of an abnormal rhythm, the device may deliver an appropriate electrical stimulation therapy to restore a more normal rhythm or in some cases withhold a therapy when the abnormal rhythm is not responsive to the therapy. For example, a pacemaker or ICD may deliver low voltage pacing pulses to the heart upon detecting bradycardia or tachycardia using endocardial or epicardial electrodes. An ICD may deliver high voltage cardioversion or defibrillation shocks to the heart upon detecting fast ventricular tachycardia or fibrillation using electrodes carried by transvenous leads or non-transvenous leads. A ventricular tachycardia therapy may be withheld when the ventricular tachycardia is determined to be a supraventricular tachycardia arising from a conducted atrial tachyarrhythmia. The type of therapy delivered and its effectiveness in restoring a normal rhythm depends at least in part on the type of electrodes used to deliver the electrical stimulation and their location relative to heart tissue. Data or information relating to the detection of an abnormal rhythm may be stored in the implantable device for uploading to an external device for diagnostic and patient monitoring purposes and for use by a clinician in selecting treatment plans.

SUMMARY

In general, the disclosure is directed to techniques for conserving electrical power required from a power supply of a medical device configured to detect cardiac arrhythmias. The disclosed techniques may be implemented in an IMD, such as a heart rhythm monitor, pacemaker or ICD, or a wearable medical device, such as a medical device incorporated in a watch, belt, band, vest or other wearable substrate. A medical device operating according to the techniques disclosed herein is configured to operate in at least two different arrhythmia monitoring states, e.g., a normal state and a power saving state. During the power saving state, less electrical power from a power source of the medical device is used than the normal state in monitoring for arrhythmias and determining a state of an arrhythmia. In some examples, power is conserved during the power saving state by at least reducing the frequency or rate of waking up a processor to analyze a cardiac electrical signal for determining a state of the arrhythmia compared to the rate of waking up the processor during the normal state. In some examples, the processor is woken up to analyze a cardiac electrical signal for determining a state of a fast atrial arrhythmias, referred to herein as "AT/AF," which may include atrial tachycardia, atrial flutter and/or atrial fibrillation.

In one example, the disclosure provides a medical device including a sensing circuit configured to sense a cardiac signal, a power source, and a control circuit including a processor powered by the power source. The control circuit is configured to operate in a normal state by waking up the processor at a first rate to analyze the cardiac signal for determining a state of an arrhythmia and switch from the normal state to a power saving state that uses less electrical power from the power source than the normal state in determining the state of the arrhythmia. Operating in the power saving state includes waking up the processor at a second rate that is less than the first rate of waking up the processor during the normal state.

In another example, the disclosure provides a method including sensing a cardiac signal, operating in a normal state by waking up a processor at a first rate to analyze the cardiac signal for determining a state of an arrhythmia; and switching from the normal state to a power saving state that uses less electrical power than the normal state in determining the state of the arrhythmia. Operating in the power saving state may include waking up the processor at a second rate that is less than the first rate of waking up the processor.

In another example, the disclosure provides a non-transitory, computer-readable storage medium comprising a set of instructions which, when executed by a control circuit of a medical device, cause the medical device to sense a cardiac signal, operate in a normal state by waking up a processor of the medical device at a first rate to analyze the cardiac signal for determining a state of an arrhythmia, and switch from the normal state to a power saving state that uses less electrical power than the normal state in determining the state of the arrhythmia. Operating in the power saving state may include waking up the processor to at a second rate that is less than the first rate of waking up the processor during the normal state.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, this disclosure describes techniques for conserving power used for detecting and monitoring cardiac arrhythmias by a medical device. In various examples, the device may be an IMD, such as an implantable cardiac monitor, pacemaker or ICD. In other examples, the medical device is an external, wearable medical device, such as an external cardiac monitor incorporated in a watch, belt, band, vest or other wearable substrate, or an external pacemaker, as examples. The medical device is configured to detect and report arrhythmias, which may or may not be treated by the medical device, e.g., by delivery of an electrical stimulation therapy. In some examples, an atrial arrhythmia may be detected which may cause withholding of a ventricular therapy, for instance.

In order to detect arrhythmias, the medical device generally senses cardiac signals to detect cyclical cardiac events and determine cardiac event intervals. The medical device processes the sensed cardiac event intervals and/or sensed event signal waveforms according to an implemented arrhythmia detection algorithm. The cardiac signal may be a cardiac electrical signal for detecting cardiac event signals attendant to myocardial depolarizations. In other examples, the medical device may sense cardiac mechanical signals attendant to myocardial contractions, e.g., from an impedance sensor, acoustical sensor, pressure sensor, accelerometer or other motion sensor, for use in detecting or confirming an arrhythmia. Processing of sensed cardiac signals can consume considerable power as electrical current is provided to power a processor executing the arrhythmia detection algorithm and/or determining a state of the arrhythmia, e.g., redetecting a sustained arrhythmia, detecting a termination of the arrhythmia, determining a rate of the arrhythmia or other arrhythmia episode information, all of which may be determined from the processed signals and stored in a memory of the medical device for reporting to a clinician for diagnostic and therapy management purposes.

Accordingly, execution of arrhythmia monitoring algorithms by a processor of a medical device drains current from the medical device power source. The useful life of an IMD for monitoring arrhythmias and/or performing other functions, e.g., for delivering cardiac pacing or other cardiac electrical stimulation therapies, which may be critical for sustaining life or maintaining quality of life, may be shortened. In an external wearable device, power consumed for arrhythmia monitoring may increase the frequency of necessary battery charging or replacement. The techniques disclosed herein conserve power used by the medical device for detecting at least some cardiac arrhythmias, e.g., atrial arrhythmias, which may not be perceived as acutely life threatening or may not be treated by the medical device but are tracked for diagnostic reporting purposes and/or discriminating from other types of more serious arrhythmias.

Figure 1:
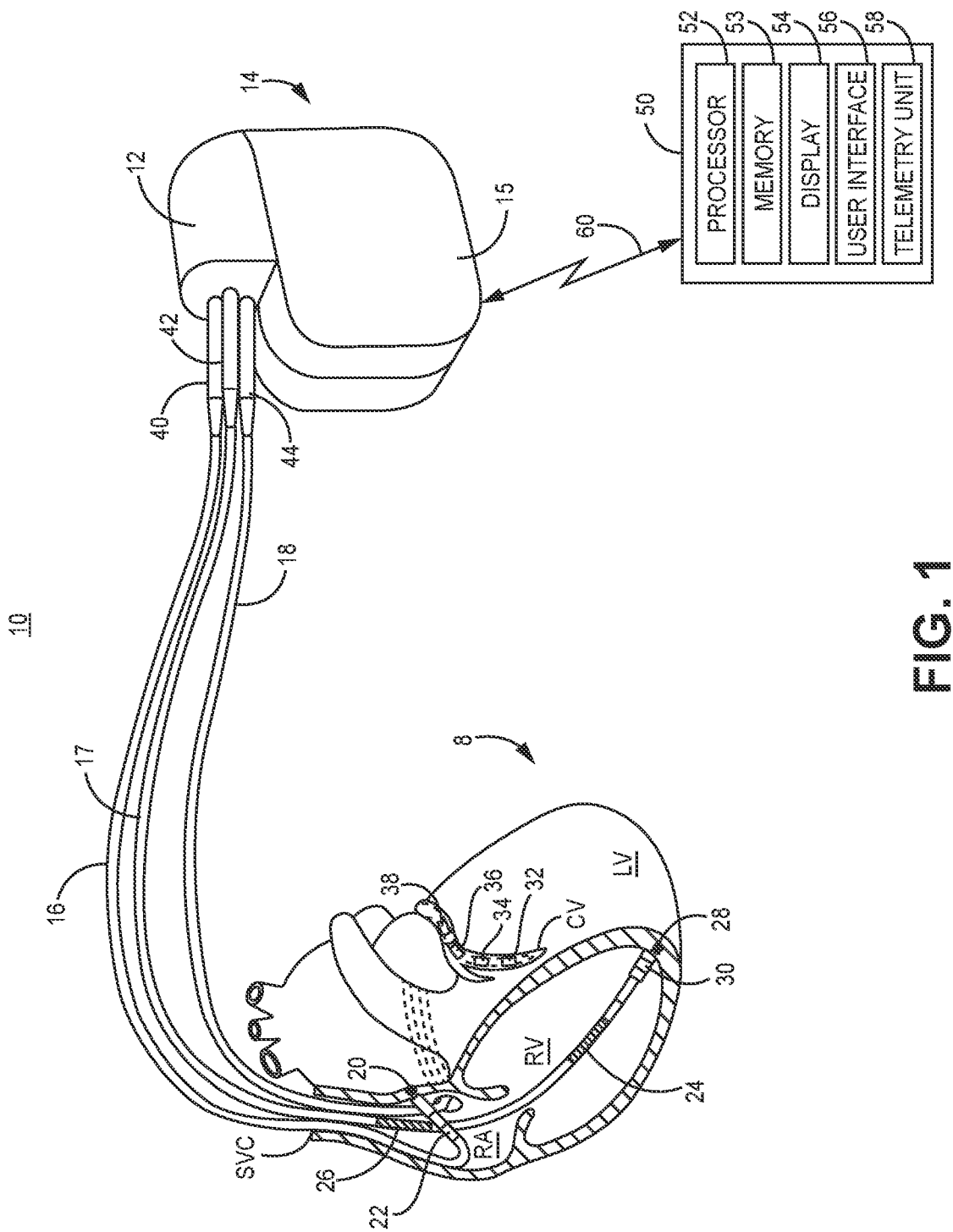
FIG. 1 is a conceptual diagram of one example of an IMD system configured to detect cardiac arrhythmias and deliver cardiac electrical stimulation therapies.

FIG. 1 is a conceptual diagram of one example of an IMD system 10 configured to detect cardiac arrhythmias and deliver cardiac electrical stimulation therapies. System 10 is capable of sensing atrial P-waves attendant to atrial myocardial depolarizations and detect AT and/or AF, referred to collectively herein as "AT/AF," based on an analysis of the sensed P-waves. AT/AF detection (also referred to herein as "atrial arrhythmia detection") methods may include an analysis of time intervals associated with P-waves, e.g., PP intervals between consecutively sensed P-waves, a ratio of P-waves to R-waves (attendant to ventricular myocardial depolarization), PR intervals, RP intervals, and/or P-wave signal morphology. According to the techniques disclosed herein, IMD system 10 is configured to operate in a normal state for sensing P-waves and detecting AT/AF and in a power saving state for sensing P-waves and detecting AT/AF. IMB 14 may switch between the normal state and the power saving state to provide detection and reporting of AT/AF episodes during both states while conserving power consumed for AT/AF detection during the power saving state compared to the normal state.

System 10 includes IMD 14 coupled to transvenous leads 16, 17 and 18 for sensing cardiac electrical signals and delivering cardiac electrical stimulation therapy in each of the right atrium (RA), right ventricle (RV) and left ventricle (LV) of heart 8. In this example, IMB 14 is configured as a multi-chamber pacemaker and defibrillator capable of delivering cardiac resynchronization therapy (CRT). CRT includes delivering pacing pulses in the LV, RV and/or RA for improving mechanical synchrony of the right and left ventricles with each other and/or with the atria, and thereby promote more efficient pumping of the heart 8. Accordingly, IMD 14 is coupled to three leads 16, 17 and 18 in this example to provide multi-chamber sensing and pacing.

Figure 3:
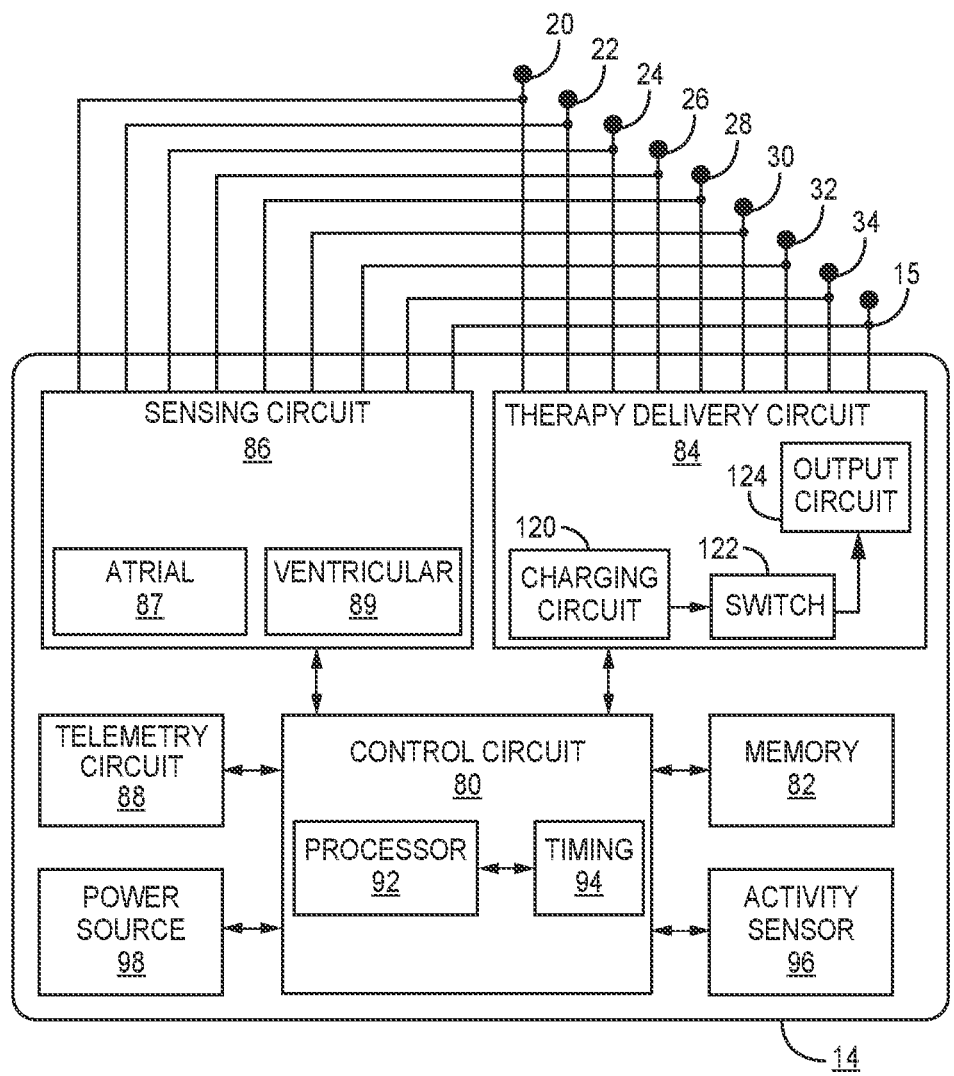
FIG. 3 is a conceptual diagram of an example configuration of a medical device that is configured to detect cardiac arrhythmias and switch between a normal state and a power saving state for detecting the cardiac arrhythmias.

IMB 14 includes a connector assembly 12 coupled to a housing 15 that encloses circuitry configured to perform IMB functions, such as a processor, cardiac electrical signal sensing circuitry and therapy delivery circuitry as further described in conjunction with FIG. 3. Connector assembly 12, sometimes referred to as a "header," is hermetically sealed to housing 15 and includes, in this example, three connector bores for receiving a proximal lead connector 40, 42 and 44 of each of the respective leads 16, 17 and 18 to provide electrical communication between electrodes carried by the distal portion of each lead and the sensing and therapy delivery circuitry enclosed by housing 15. Housing 15 is formed from a biocompatible material, such as a stainless steel or titanium alloy. In some examples, the housing 15 may include an insulating coating over at least outer portions of housing 15. Examples of insulating coatings include parylene, urethane, PEEK, or polyimide among others. Housing 15 may be hermetically sealed to enclose IMD circuitry and protect IMD circuitry from blood and body fluids.

Leads coupled to IMD 14 include RA lead 16, RV lead 17 and a coronary sinus (CS) lead 18. RA lead 16 may carry a distal tip electrode 20 and ring electrode 22 spaced proximally from tip electrode 20 for sensing atrial electrical signals, e.g., P-waves, and delivering RA pacing pulses. RA lead 16 may be positioned such that its distal end is in the vicinity of the RA and the superior vena cava and includes insulated electrical conductors extending through the elongated lead body from each of electrodes 20 and 22 to the proximal lead connector 40.

RV lead 17 includes pacing and sensing electrodes 28 and 30 shown as a tip electrode 28 and a ring electrode 30 spaced proximally from tip electrode 28. The electrodes 28 and 30 provide sensing and pacing in the RV and are each connected to a respective insulated conductor within the body of RV lead 17. Each insulated conductor is coupled at its proximal end to proximal lead connector 42. RV lead 17 is positioned such that its distal end is in the RV for sensing RV electrical signals, such as R-waves attendant to ventricular depolarizations, and delivering pacing pulses in the RV. In some examples, IMD 14 is capable of delivering high voltage pulses for cardioverting or defibrillating heart 8 in response to detecting a tachyarrhythmia. In this case, RV lead 17 may include defibrillation electrodes 24 and 26, which may be elongated coil electrodes used to deliver high voltage cardioversion/defibrillation (CV/DF) therapy, also referred to a "shocks" or "shock pulses."

Defibrillation electrode 24 may be referred to as the "RV defibrillation electrode" or "RV coil electrode" because it is carried along the body of RV lead 17 such that it is positioned substantially within the RV when distal pacing and sensing electrodes 28 and 30 are positioned for pacing and sensing in the RV. For example, Tip electrode 28 may be positioned at an endocardial location of the RV apex. Defibrillation electrode 26 may be referred to as a "superior vena cava (SVC) defibrillation electrode" or "SVC coil electrode" because it is carried along the body of RV lead 17 such that it is positioned at least partially along the SVC when the distal end of RV lead 17 is advanced within the RV. While electrodes 24 and 26 are referred to herein as defibrillation electrodes, it is to be understood that electrodes 24 and 26 may be used for sensing cardiac electrical signals, delivering cardiac pacing pulses or delivering anti-tachycardia pacing (ATP) therapy and are not necessarily limited to only being used for delivering high voltage CV/DV shock pulses. Each of electrodes 24, 26, 28 and 30 are connected to a respective insulated conductor extending within the body of lead 17. The proximal end of the insulated conductors are coupled to corresponding connectors carried by proximal lead connector 42, e.g., a DF-4 connector, at the proximal end of lead 17 for providing electrical connection to IMD 14.

CS lead 18 may be advanced within the vasculature of the left side of the heart via the coronary sinus and a cardiac vein (CV). CS lead 18 is shown as a quadripolar lead having four electrodes 32, 34, 36 and 38 that may be selected in various bipolar or unipolar electrode vectors for sensing cardiac electrical signals from the LV and delivering cardiac pacing pulses to the LV, e.g., during CRT delivery. In other examples, CS lead 18 may include one or more electrodes for sensing cardiac electrical signals and delivering pacing pulses to the LV. The electrodes 32, 34, 36 and 38 are each coupled to respective insulated conductors within the body of CS lead 18, which provides electrical and mechanical connection to the proximal lead connector 44, coupled to IMD connector assembly 12.

The various pacing and sensing electrodes 20, 22, 28, 30, 32, 34, 36 and 38 may be selected in bipolar combinations for sensing and pacing in the respective RA, RV or LV. In some examples, housing 15 may be used as an electrode, sometimes referred to as a "can" electrode, for selection in a unipolar pacing or sensing electrode vector with any of electrodes 20, 22, 28, 30, 32, 34, 36 or 38. The IMD housing 15 may serve as a subcutaneous defibrillation electrode in combination with one or both of RV coil electrode 24 and SVC coil electrode 26 for delivering CV/DF shocks to heart 8. It is recognized that numerous sensing and electrical stimulation electrode vectors may be available using the various electrodes carried by one or more of leads 16, 17 and 18.

It is recognized that alternate lead systems may be substituted for the three lead system illustrated in FIG. 1. While a particular multi-chamber IMD and lead system is illustrated in FIG. 1, techniques disclosed herein may be implemented in a single chamber, dual chamber or multi-chamber cardiac pacemaker, which may or may not include CRT or CV/DF capabilities. Such devices may be coupled to one or more transvenous leads, such as leads 16, 17 and 18, which may each be used to position electrodes in one or more heart chambers. In some examples, a single lead may include both ventricular electrodes and one or more atrial electrodes for sensing and stimulating in the ventricle and for sensing in the atrium. In other examples, non-transvenous or extracardiac leads that extend subcutaneously, submuscularly or substernally may be used to place electrodes and/or other sensors for sensing cardiac signals and detecting arrhythmias therefrom. Examples of other IMDs, such as an extracardiovascular IMD system, in which the techniques disclosed herein may be implemented are generally disclosed in U.S. Pat. No. 10,045,710 (Higgins, et al.), incorporated herein by reference in its entirety.

An external device 50 is shown in wireless telemetric communication with IMD 14 via a communication link 60. Communication link 60 may be established using a radio frequency (RF) link such as BLUETOOTH®, Wi-Fi, Medical Implant Communication Service (MICS) or other communication bandwidth. External device 50 may be referred to as a "programmer" used by a physician, technician, nurse, clinician or other qualified user for programming operating parameters in IMB 14. External device 50 may be located in a clinic, hospital or other medical facility. External device 50 may alternatively be embodied as a home monitor or a handheld device that may be used in the patient's home or another location to allow a patient or other user to interact with IMD 14 or remote monitoring of the patient and IMB 14 operations. External device 50 may correspond to the MYCARELINK™ Patient Monitor available from Medtronic, Inc. Minneapolis Minn., USA, in one example.

IMD operating parameters, such as sensing and therapy delivery control parameters, may be programmed into IMB 14 using external device 50. External device 50 includes an external processor 52, memory 53, user display 54, user interface 56 and telemetry unit 58. External processor 52 controls external device operations and processes data and signals received from IMB 14. External processor 52 provides user display 54 with therapy delivery data, cardiac electrical signal data, cardiac arrhythmia episode data, such as AT/AF data, and/or other device- or patient-related data retrieved from IMD 14 for generating a display of the data for observation and review by a clinician.

The user display 54 generates a display of data received from IMB 14 and may include a graphical user interface that facilitates programming of one or more sensing parameters, arrhythmia detection parameters, therapy delivery parameters and the like by a user interacting with external device 50. External device 50 may display other data and information relating to IMD functions to a user for reviewing IMD operation and programmed parameters as well as cardiac electrical signals or other physiological data that is retrieved from IMB 14 during an interrogation session. User interface 56 may include a mouse, touch screen, or other pointing device, keyboard and/or keypad to enable a user to interact with external device 50 to initiate a telemetry session with IMD 14 for retrieving data from and/or transmitting data to IMD 14 and for selecting and programming desired sensing and therapy delivery control parameters, tachyarrhythmia detection algorithms and other operating parameters into IMB 14. According to the techniques disclosed herein, normal state and power saving state operating parameters for detecting cardiac arrhythmias may be programmed using external device 50.

External telemetry unit 58 includes a transceiver and antenna configured for bidirectional communication with an implantable transceiver and antenna included in IMB 14. In some examples, external device 50 may include a programming head that is placed proximate IMB 14 to establish and maintain a communication link, and in other examples external device 50 and IMD 14 may be configured to communicate using a distance telemetry algorithm and circuitry that does not require the use of a programming head and does not require user intervention to maintain a communication link. It is contemplated that external device 50 may be in wired or wireless connection to a communications network via telemetry unit 58 for transferring data to a centralized database or computer to allow remote management of the patient. Remote patient management systems may be configured to utilize the presently disclosed techniques to enable a clinician to review cardiac electrical signal data, atrial tachyarrhythmia episode data and AT/AF detection operating states received from IMB 14.

Figure 2:
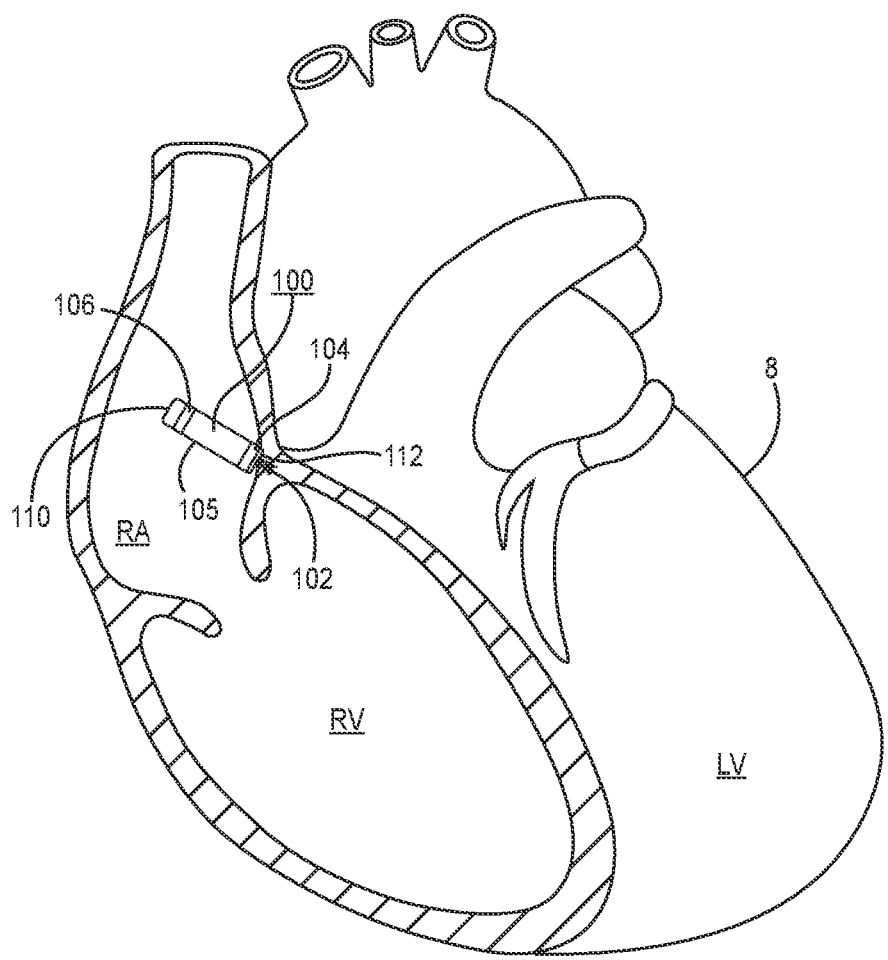
FIG. 2 is a conceptual diagram of a leadless intra-cardiac pacemaker positioned within the right atrium for sensing atrial signals and delivering cardiac pacing pulses.

FIG. 2 is a conceptual diagram of a leadless intra-cardiac pacemaker positioned within the right atrium for sensing atrial signals and delivering cardiac pacing pulses to heart 8. Pacemaker 100 may be configured to sense P-waves and deliver atrial pacing pulses in the absence of a sensed P-wave. Pacemaker 100 may be a leadless pacemaker including a housing 105 enclosing pacemaker circuitry. Pacemaker 100 may include two or more housing-based electrodes 102, 104 and 106. Distal tip electrode 102 may be a button, spherical or helical electrode extending from the distal end 112 of pacemaker 100. One or more ring electrodes 104 and 106 may be provided along the longitudinal sidewall of housing 105, e.g., circumscribing a generally cylindrical housing 105. Electrode 104 is shown adjacent distal end 112, and electrode 106 is shown spaced apart proximally, adjacent the proximal end 110 of pacemaker 100. Distal tip electrode 104 may be used as a pacing cathode electrode with either of ring electrodes 104 and 106 as the return anode. Electrodes 104 and 106 may be used for sensing atrial signals, as a bipolar pair or paired with tip electrode 102.

Tip electrode 102 may be deployed in atrial myocardial tissue to provide single chamber atrial sensing and pacing by pacemaker 100. In other examples, tip electrode 102 may be positioned in or near the bundle of His for delivering pacing pulses to the native ventricular conduction system to provide ventricular pacing. In this case, atrial and ventricular signals may be sensed by pacemaker 100, and ventricular pacing may be delivered, which may be synchronized to atrial P-waves.

Electrodes 102, 104 and 106 may be positioned at locations along pacemaker 100 other than the locations shown. Electrodes 102, 104 and 106 (as well as the electrodes carried by leads 16, 17 and 18 shown in FIG. 1) may be, without limitation, titanium, platinum, iridium or alloys thereof and may include a low polarizing coating, such as titanium nitride, iridium oxide, ruthenium oxide, platinum black among others. Housing 105 is formed from a biocompatible material, such as a stainless steel or titanium alloy. In some examples, the housing 105 may include an insulating coating. Examples of insulating coatings include parylene, urethane, PEEK, or polyimide among others. The entirety of the housing 105 may be insulated, but only electrodes 102, 104 and 106 uninsulated.

Pacemaker 100 is configured to sense atrial P-waves and detect AT/AF by analyzing time intervals associated with sensed P-waves and/or P-wave morphology. As disclosed herein, pacemaker 100 may switch between at least two different atrial arrhythmia detection operating states, e.g., a normal state and a power saving state. During the power saving state, atrial sensing, the rate of waking up a processor for processing of atrial signals, and/or the number of steps or criteria analyzed for detecting AT/AF may be reduced to conserve electrical power consumed in detecting atrial arrhythmias, thereby extending the useful life of the power supply of pacemaker 100 compared to AT/AF detection without a power saving state.

While pacemaker 100 is shown within the RA, it is to be understood that a leadless pacemaker may be positioned in or on the heart 8 for sensing cardiac signals and detecting arrhythmias. The power saving techniques disclosed herein are not limited to use with a medical device having atrial electrodes placed within the RA as shown in FIGS. 1 and 2 but may be implemented in a variety of medical devices having electrodes and/or sensors configured to sense cardiac signals and detect arrhythmias therefrom. In some examples, sensing of atrial P-waves is not required for detecting atrial arrhythmias. For example, atrial arrhythmias may be detected from an analysis of RR interval variability, where each RR interval is the time interval between two consecutively sensed R-waves from a cardiac electrical signal. The power saving state techniques disclosed herein may be implemented in a device performing arrhythmia detection using ventricular signals as generally disclosed in U.S. Pat. No. 7,623,911 B2 (Sarkar, et al.) and U.S. Pat. No. 9,486,155 B2 (Sarkar, et al.), both of which are incorporated herein by reference in their entirety. The techniques disclosed herein employing a power saving state to reduce power consumed for monitoring an arrhythmia may be implemented in conjunction with any arrhythmia detection technique that utilizes processing circuitry for determining a state of the arrhythmia.

FIG. 3 is a conceptual diagram of an example configuration of a medical device that is configured to detect cardiac arrhythmias and switch between a normal state and a power saving state for detecting the cardiac arrhythmias. The circuitry shown in FIG. 3 is described with reference to the multi-chamber IMD 14 of FIG. 1, having sensing, pacing and cardioversion/defibrillation capabilities and coupled to three leads carrying electrodes 20, 22, 24, 26, 28, 30, 32 and 34 (and 36 and 38, not shown in FIG. 3). However, it is to be understood that the circuits and components shown and described in conjunction with FIG. 3 may be included in pacemaker 100 of FIG. 2 or other cardiac rhythm monitoring or therapy delivery IMDs or wearable medical devices to provide the functionality disclosed herein for switching between a normal state and power saving state for monitoring for and detecting cardiac arrhythmias.

The techniques disclosed herein are primarily described with regard to a power saving state for monitoring and detection atrial tachyarrhythmia, e.g., AT/AF. AT/AF may not be treated by electrical stimulation therapies delivered by the IMD. However, AT/AF may be monitored to provide important cardiac rhythm information and data to a clinician caring for the patient. Atrial tachyarrhythmia may not be immediately life threatening but may be an important diagnostic and prognostic condition that improves the clinician's ability to manage the patient, e.g., with prescription drugs, IMDs or otherwise, for avoiding more serious arrhythmias and stroke. Accordingly, physicians may expect an IMD capable of monitoring cardiac rhythms to provide AT/AF information but without significantly reducing the useful life of the IMD for providing more critical ventricular tachyarrhythmia monitoring and detection and/or cardiac pacing therapy delivery and CV/DF shocks. As such, the operating states for monitoring and detecting cardiac arrhythmias are described as being used for AT/AF detection, however, it is contemplated that aspects disclosed herein for switching between a normal and a power saving state and techniques for reducing power consumption during the power saving state compared to the normal state in detecting arrhythmias may be used for monitoring and detecting other types of arrhythmias, including ventricular tachyarrhythmia in some examples.

IMD 14 includes a control circuit 80, memory 82, therapy delivery circuit 84, a cardiac signal sensing circuit 86 (also referred to herein as "sensing circuit 86"), telemetry circuit 88, activity sensor 96 and a power source 98. The various circuits represented in FIG. 3 may be combined on one or more integrated circuit boards which include a specific integrated circuit (ASIC), an electronic circuit, a processor (shared, dedicated, or group) and memory that execute one or more software or firmware programs, a combinational logic circuit, state machine or other suitable components that provide the described functionality.

Cardiac signal sensing circuit 86 may include multiple sensing channels, e.g., an atrial sensing channel 87 and a ventricular sensing channel 89. Atrial sensing channel may be configured to receive a cardiac electrical signal, e.g., via RA electrodes 20 and 22, for sensing atrial P-waves and producing an atrial EGM signal that may be passed to control circuit 80 for analysis by processor 92 for atrial arrhythmia detection. A ventricular sensing channel 89 may receive a cardiac electrical signal, e.g., via RV electrodes 24 and 26 and/or CS electrodes 32, 34, 36 and 38 (only electrodes 32 and 34 are shown in FIG. 3 for the sake of clarity). Ventricular sensing channel 89 includes circuitry for detecting ventricular R-waves and for producing a ventricular EGM signal that may be passed to control circuit 80 for use in detecting ventricular arrhythmias. When IMD 14 is a multi-chamber device, separate RV and LV sensing channels may be provided for sensing ventricular electrical signals from the respective RV electrodes 24 and 26 and CS electrodes 32, 34, 36 and 38.

Each atrial sensing channel 87 and ventricular sensing channel 89 may include a respective pre-filter and amplifier circuit including a high pass filter to remove DC offset, e.g., a 2.5 to 5 Hz high pass filter, or a wideband filter having a passband of 2.5 Hz to 100 Hz to remove DC offset and high frequency noise. The pre-filter and amplifier circuit may further include an amplifier to amplify a "raw" cardiac electrical signal that is passed to an analog-to-digital convertor (ADC) included in each sensing channel 87 and 89. The ADC may pass a multi-bit, digital EGM signal to control circuit 80 for use in detecting cardiac events and determining a patient's heart rhythm. The digital signal from the ADC of each respective channel 87 and 89 may be passed to a rectifier and amplifier circuit included in sensing circuit 86, which may include a rectifier, bandpass filter, and amplifier for passing the filtered and rectified cardiac electrical signal to a respective cardiac event detector, e.g., a P-wave detector in the atrial channel 87 and an R-wave detector in the ventricular channel 89.

The cardiac event detector of each respective channel 87 and 89 may include a sense amplifier or other detection circuitry that compares the incoming rectified, cardiac electrical signal to a cardiac event sensing threshold amplitude, which may be an auto-adjusting threshold. When the incoming signal crosses the sensing threshold amplitude the cardiac event detector produces a cardiac sensed event signal that is passed to control circuit 80. R-wave sensed event signals may be passed from ventricular sensing channel 89 to control circuit 80 in response to an R-wave detector sensing an R-wave. R-wave sensed event signals may be used by timing circuit 94 for scheduling ventricular pacing pulses and determining ventricular rate intervals or RR intervals (between two consecutively received R-wave sensed event signals). Control circuit 80 may determine the ventricular rhythm from the determined RR intervals, which may be in combination with an analysis performed by processor 92 of the ventricular EGM signal received from sensing circuit 86.

Control circuit 80 may receive P-wave sensed event signals from atrial sensing channel 87 each time the P-wave detector included in atrial sensing channel 87 senses an atrial P-wave due to a P-wave sensing threshold crossing by the atrial signal received via electrodes 20 and 22. P-wave sensed event signals may be used by timing circuit 94 in scheduling atrial and/or ventricular pacing pulses and determining the atrial rate by determining PP intervals between consecutively received P-wave sensed event signals. Processor 92 is configured to perform an atrial arrhythmia detection algorithm, e.g., by executing instructions stored in memory 82, which may include an analysis of PP intervals (and/or other cardiac event intervals such as PR intervals, RP intervals and RR intervals) and/or atrial EGM signal morphology. Control circuit 80 is configured to "wake up" processor 92 to process the atrial signal information for AT/AF detection or for determining a state of a detected AT/AF episode. As used herein, the term "wake up" with regard to processor 92 refers to a power control operation during which electrical current or power is provided from power source 98 to processor 92 to enable it to perform processing functions. When not powered up for performing processing functions, processor 92 may be put to "sleep" by withholding or minimizing the electrical current applied to processor 92.

While examples of AT/AF detection described herein generally refer to sensing of P-waves and/or R-waves from cardiac electrical signals for AT/AF detection, it is recognized that sensing circuit 86 may include or be coupled to other sensors for sensing cardiac signals, detecting cyclical cardiac events, e.g., corresponding to atrial systole and/or ventricular systole, and producing cardiac sensed event signals and/or signal waveforms that are passed to control circuit 80 for use in detecting AT/AF. Sensing circuit 86 may therefore be configured to sense cardiac mechanical signals and/or cardiac electrical signals for use in detecting arrhythmias. Sensing circuit 86 may sense impedance signals using the electrodes coupled to sensing circuit 86. In other examples, sensing circuit 86 may include or be coupled to an acoustical sensor, motion sensor, pressure sensor or other mechanical sensor that is enclosed by the IMD housing 15, mounted on housing 15, or carried by a lead coupled to sensing circuit 86 for producing a cardiac signal.

As disclosed herein, control circuit 80 may operate according to a normal operating state during which control circuit 80 wakes up processor 92 at a rate or frequency based on wake up criteria established for the normal state. In some examples, the rate of waking up processor 92 during the normal state may be as often as each time an atrial sensed event signal, e.g., a P-wave sensed event signal, is received from atrial sensing channel 87. Control circuit 80 is further configured to switch between the normal operating state and a power saving state during which control circuit 80 may reduce the frequency or rate of waking up processor 92 for the purpose of performing an atrial arrhythmia detection algorithm or determine a state of an atrial arrhythmia. During the power saving state, control circuit 80 may additionally or alternatively adjust sensing control parameters used by atrial sensing channel 87 to reduce current from power source 98 required for sensing atrial P-waves (or atrial mechanical events). For example, amplifiers, an ADC, filters or other circuitry in atrial sensing channel 87 may be disabled or disconnected from power source 98. In some examples, P-wave sensing control parameters are adjusted to intentionally cause P-wave undersensing and effectively reduce the frequency or rate of processor 92 wake ups for the purposes of atrial signal processing for atrial arrhythmia detection.

Control circuit 80 includes timing circuit 94 and processor 92. Control circuit 80 may receive P-wave sensed event signals, R-wave sensed event signals and/or digital cardiac electrical signals from sensing circuit 86 for use in detecting cardiac arrhythmias and controlling therapy delivery functions. For example, P-wave sensed events signals and R-wave sensed event signals may be passed to timing circuit 94 for inhibiting scheduled atrial or ventricular pacing pulses, respectively. Timing circuit 94 may set pacing escape intervals in response to a cardiac sensed event signal. For example, an atrial pacing escape interval may be started in response to a P-wave sensed event signal. A ventricular pacing escape interval may be started in response to an R-wave sensed event signal or a P-wave sensed event signal. Expiration of the pacing escape interval causes therapy delivery circuit 84 to deliver a pacing pulse to the appropriate cardiac chamber via a pacing electrode vector selected from the available electrodes. If a cardiac event signal is received prior to expiration of the pacing escape interval, the time that has expired on the pacing escape interval timer or counter is determined as a cardiac event interval, e.g., a PP interval or RR interval. The cardiac event intervals determined by timing circuit 94 may be used by processor 92 for detecting arrhythmias such as AT/AF.

Control circuit 80 may retrieve programmable therapy delivery control parameters from memory 82, such as pacing rate as controlled by timing circuit and pacing pulse amplitude, pacing pulse width, and CV/DF shock energy, which are passed to therapy delivery circuit 84 for controlling electrical stimulation pulse delivery. In addition to providing control signals to therapy delivery circuit 84, control circuit 80 may provide sensing control signals to sensing circuit 86, e.g., P-wave and R-wave sensing thresholds, sensitivity, and/or various blanking and refractory intervals applied to the cardiac electrical signal to control sensing of P-waves and R-waves by the respective atrial channel 87 and ventricular channel 89.

Therapy delivery circuit 84 generates electrical pacing pulses that are delivered to the patient's heart via the available electrodes coupled to IMD 14, e.g., electrodes 20, 22, 24, 26, 28, 30, 32, 34, 36 and 38 and housing 15. Therapy delivery circuit 84 may include charging circuit 120, switching circuit 122 and an output circuit 124. Charging circuit 120 may include one or more holding capacitors that may be charged to a pacing pulse amplitude by a multiple of the battery voltage signal of power source 98 under the control of a voltage regulator. The pacing pulse amplitude may be set based on a control signal from control circuit 80. Switching circuit 122 may control when the holding capacitor of charging circuit 120 is coupled to the output circuit 124 for delivering the pacing pulse. For example, switching circuit 122 may include a switch that is activated by a timing signal received from timing circuit 94 upon expiration of a pacing escape interval and kept closed for a programmed pacing pulse width to enable discharging of the holding capacitor of charging circuit 120. The holding capacitor, previously charged to the pacing pulse voltage amplitude, is discharged across a selected electrode pacing vector through an output capacitor of output circuit 124 for the programmed pacing pulse duration. Output circuit may include multiple output capacitors and switching circuitry for selectively discharging the holding capacitor through a desired output capacitor and pacing electrode vector. Examples of pacing circuitry generally disclosed in U.S. Pat. No. 5,507,782 (Kieval, et al.) and in U.S. Pat. No. 8,532,785 (Crutchfield, et al.), both of which patents are incorporated herein by reference in their entirety, may be implemented in pacemaker 14 for charging a pacing capacitor to a predetermined pacing pulse amplitude under the control of control circuit 80 for generating and delivering a pacing pulse.

Therapy delivery circuit 84 may include both high voltage holding capacitor(s) and low voltage capacitor(s) in charging circuit 120 when IMD 14 is capable of delivering high voltage CV/DF shock therapies in addition to cardiac pacing therapies. For example, a high voltage holding capacitor may be charged to a voltage corresponding to a programmed shock energy using a transformer. As such, charging circuit 120 may include a transformer to step up the battery voltage of power source 98 in order to achieve charging of a high voltage rated capacitor to a voltage that is much greater than the battery voltage. Charging of the high voltage capacitor (or a combination of capacitors) by charging circuit 120 may be performed under the control of processor 92, which receives feedback signals from therapy delivery circuit 84 for determining when the high voltage capacitor is charged to a voltage corresponding to a programmed shock energy. A charge completion signal may be passed from processor 92 to charging circuit 120 to terminate charging. One example of a high voltage charging circuit and its operation is generally disclosed in U.S. Pat. No. 8,195,291 (Norton, et al.), incorporated herein by reference in its entirety.

Pacemaker 14 may include one or more sensors for monitoring physiological signals of the patient other than the cardiac electrical signals sensed by sensing circuit 86. For example, IMD 14 may include a patient activity sensor 96 which may include a motion sensor such as an accelerometer for detecting motion of the patient caused by patient physical activity. A signal from activity sensor 96 passed to control circuit 80 may be analyzed by processor 92 for determining a metric of patient physical activity for use in controlling the pacing rate according to the patient's physical activity level, sometimes referred to as "rate responsive pacing." In some examples, processor 92 is woken up at predetermined time intervals to determine a patient activity metric, which may be determined by determining a threshold crossing count and/or integration of the motion sensor signal. For instance, processor 92 may be woken up at two second time intervals by control circuit 80 to determine an updated patient activity metric from the activity sensor signal, determine an updated sensor indicated pacing rate, and adjust the pacing rate intervals accordingly.

In other examples, IMD 14 may include other sensors in addition to or instead of activity sensor 96, such as a pressure sensor, optical sensor, acoustical sensor, temperature sensor, pH sensor, or any combination thereof. Processor 92 may determine a metric correlated to a patient condition from a sensor signal or combination of sensor signals for determining patient-related diagnostic data that may be stored in memory 82 and/or used for controlling therapy delivered by therapy delivery circuit 84.

Memory 82 may include computer-readable instructions that, when executed by processor 92 of control circuit 80, cause control circuit 80 to perform various functions attributed throughout this disclosure to IMD 14 (or pacemaker 100). The computer-readable instructions may be encoded within memory 82. Memory 82 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media.

Power source 98 provides power to each of the other circuits and components of IMD 14 as required. Power source 98 may include one or more energy storage devices, such as one or more rechargeable or non-rechargeable batteries. The connection between power source 98 and control circuit 80 is shown, but connections between power source 98 and other circuits and components are not shown in FIG. 3 for the sake of clarity and are to be understood from the general block diagram of FIG. 3. For example power source 98 may provide power to charging circuit 120 for charging a holding capacitor to a pacing voltage amplitude, current to switch 122 and other circuitry included in therapy delivery circuit 84 as needed to generate and deliver electrical stimulation pulses to the patient's heart. Power source 98 also provides power to telemetry circuit 88, sensing circuit 86 and activity sensor 96 as needed as well as memory 82. As described herein, control circuit 80 may control when power source 98 is coupled to processor 92 and atrial sensing channel 87 according to a power saving state to reduce current drain of power source 98 required for detecting and monitoring AT/AF.

IMD 14 may include a telemetry circuit 88 including a transceiver and antenna for transferring and receiving data, e.g., via a radio frequency (RF) communication link with an external programmer or home monitor, such as external device 50 shown in FIG. 1. Telemetry circuit 88 may be capable of bi-directional communication with external device 50 (FIG. 1), for example, when external device 50 is a programmer or home monitor used to transmit programming commands to IMD 14 and retrieve data from IMD 14. Cardiac electrical signals, marker channel data depicting the timing of cardiac event sensing and pacing, currently programmed parameters or other data may be transmitted by telemetry circuit 88. In particular, cardiac signal episodes representative of detected arrhythmias including episodes of AT/AF may be stored in memory 82 and transmitted via telemetry circuit 88. Programmable control parameters and programming commands for controlling cardiac electrical signal sensing and cardiac pacing may be received by telemetry circuit 88 and stored in memory 82 for access by control circuit 80.

The functions attributed to a medical device herein may be embodied as one or more processors, controllers, hardware, firmware, software, or any combination thereof. Depiction of different features as specific circuitry is intended to highlight different functional aspects and does not necessarily imply that such functions must be realized by separate hardware, firmware or software components or by any particular circuit architecture. Rather, functionality associated with one or more circuits described herein may be performed by separate hardware, firmware or software components, or integrated within common hardware, firmware or software components. The operation of circuitry included a medical device as disclosed herein should not be construed as reflective of a specific form of hardware, firmware and software necessary to practice the techniques described. It is believed that the particular form of software, hardware and/or firmware will be determined primarily by the particular system architecture employed in the medical device and by the particular sensing and therapy delivery circuitry employed by the medical device. Providing software, hardware, and/or firmware to accomplish the described functionality in the context of any modern medical device, given the disclosure herein, is within the abilities of one of skill in the art. For example, processor 92 may be configured to execute firmware stored in memory 82 for detecting AT/AF while P-wave sensing, PP interval determination or counts of P-wave sensed event signals may be implemented in hardware included in sensing circuit 86 and control circuit 80.

Figure 4:
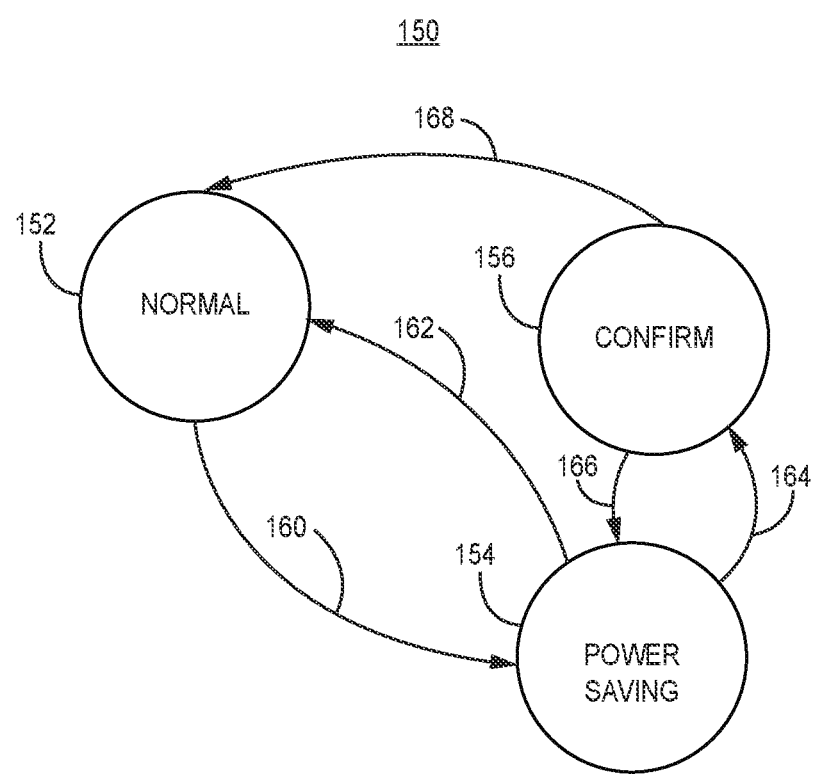
FIG. 4 is a conceptual diagram of arrhythmia detection operating states that an IMD control circuit may switch between according to some examples.

FIG. 4 is a conceptual diagram 150 of arrhythmia detection operating states that the control circuit 80 may switch between according to some examples. The IMB performing the techniques disclosed herein may be configured to operate in at least a normal atrial arrhythmia detection state 152, also referred to herein as "normal state" 152, and a power saving atrial arrhythmia detection state 154, also referred to herein as "power saving state" 154. The control circuit 80 may switch from the normal state 152 to the power saving state 154 (path 160) when conditions or criteria for conserving power required for detecting atrial arrhythmias are satisfied. Conditions for switching to the power saving state are described below, e.g., in conjunction with FIG. 5, and may include a threshold duration of time operating in the normal state, a threshold duration of a detected AT/AF episode, or a threshold duration of no atrial sensing, as examples. During the power saving state, one or more operations may be suspended or reduced in frequency to reduce the power consumed for detection of atrial arrhythmias. Atrial arrhythmias, however, may still be detected or monitored during the power saving state. Atrial arrhythmia monitoring may not be fully disabled during the power saving state. However, the power used for detecting arrhythmias during the power saving state 154 is less than the power used for detection of arrhythmias during the normal state 152.

Control circuit 80 may switch from the power saving state 154 directly back to the normal state 152 (path 162) when conditions or criteria for returning to the normal state 152 are met. In some examples, one condition for switching back to the normal state may be a maximum time duration spent in the power saving state 154. Other examples of conditions or criteria for switching between the normal state 152 and the power saving state 154 are described below in conjunction with the various flow charts presented herein.

In some examples, control circuit 80 may switch from the power saving state 154 to a third, confirm state 156 (path 164). During the confirm state 156, the IMD may determine whether conditions that caused the control circuit 80 to switch to the power saving state are still satisfied. If a condition that caused control circuit 80 to switch to the power saving state 154 from the normal state 152 is still present, control circuit 80 may switch back to the power saving state 154 from confirm state 156 (pathway 166). If not, control circuit 80 may switch from the confirm state 156 to the normal state 152 (pathway 168). In other examples, control circuit 80 may determine if other criteria are met for switching from the confirm state 156 to the normal state 152. If criteria for returning to the normal state are unmet, control circuit 80 switches from the confirm state 156 back to the power saving state 154. Example operations performed during the various normal state 152, power saving state 154 and confirm state 156 are described below in conjunction with the flow charts of FIGS. 5-7.

Figure 5:
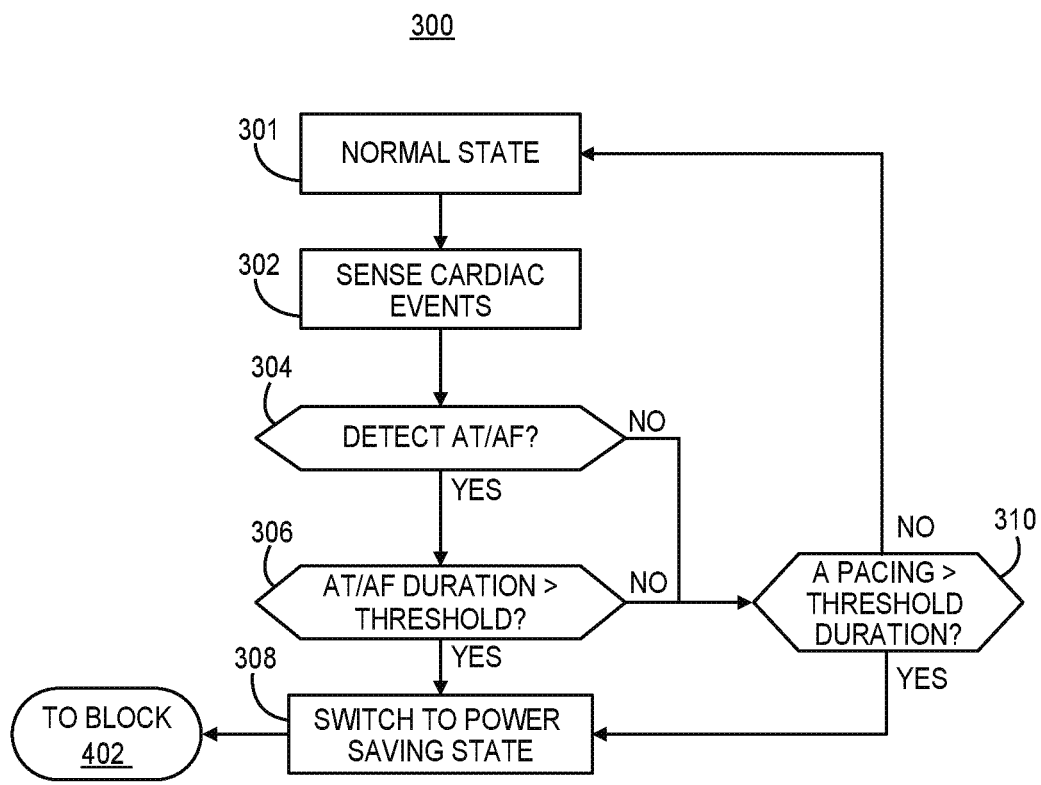
FIG. 5 is a flow chart of operations performed by a medical device for detecting atrial arrhythmias during a normal operating state according to one example.

FIG. 5 is a flow chart 300 of operations performed by an IMD for detecting atrial arrhythmias while operating in the normal state 152 of FIG. 4 according to one example. At block 301, control circuit 80 enters the normal state for controlling processor 92 to execute an atrial arrhythmia detection algorithm according to the normal state. At block 302, cardiac events are sensed for use in detecting atrial arrhythmias. The techniques disclosed herein refer to cardiac events being sensed from cardiac electrical signals received by sensing circuit 86, however it is contemplated that cardiac mechanical signals may also be sensed for use in arrhythmia detection. In some examples, control circuit 80 wakes up processor 92 upon receipt of each atrial sensed event signal, e.g., a P-wave signal received from sensing circuit 86. Processor 92 analyzes the PP interval, the P-wave morphology and/or specified P-wave features along with stored P-wave data, e.g., preceding PP intervals and/or P-wave morphologies, according to an implemented AT/AF detection algorithm. For example, control circuit 80 may detect AT/AF in response to a predetermined number of PP intervals being less than a detection time interval. Upon being woken up in response to each P-wave sensed event signal, processor 92 determines if the most recent PP intervals satisfy the detection criteria, which may be N out of the most recent N consecutive PP intervals or N out of the most recent M PP intervals, where M is greater than N such that the threshold number N PP intervals that are less than the detection interval do not have to be consecutive. In other examples, processor 92 may determine if a threshold number of RR intervals include evidence of an atrial arrhythmia, e.g., multiple P-waves sensed by an atrial channel during a single RR interval. To illustrate, if at least 40 consecutive RR intervals each include two or more P-waves sensed during the RR interval, AT/AF may be detected.

If AT/AF is detected at block 304 according to detection criteria applied by processor 92, control circuit 80 may determine if one or more conditions for switching to the power saving state are satisfied. At block 306, control circuit 80 may determine if the detected AT/AF episode has reached a threshold time duration ("yes" branch of block 306) to warrant switching to the power saving state at block 308. When a patient is experiencing a sustained AT/AF episode or chronic AT/AF, an AT/AF detection algorithm performed by processor 92 upon each P-wave sensed event signal consumes processing power that is not detecting a change in the patient's atrial rhythm. Accordingly, control circuit 80 may switch to the power saving state to reduce the power consumed to monitor the patient's atrial rhythm during the sustained AT/AF episode. An AT/AF episode duration threshold causing control circuit 80 to switch to the power saving state may be 30 seconds, one minute, several minutes, one hour, several hours, one day, or several days, as examples.

If AT/AF is not detected at block 304, or if a detected AT/AF episode has not yet reached a threshold duration ("no" branch of block 306), control circuit 80 may apply other criteria for determining whether to remain in the normal state or switch to the power saving state. For example, control circuit 80 may determine at block 310 if no atrial events have been sensed for a threshold duration, e.g., associated with sustained atrial pacing for a threshold duration. A threshold number of pacing pulses delivered without atrial sensed events or a threshold ratio of atrial pacing to atrial sensed events may define power saving state switching criteria. In various illustrative examples, if at least 80%, 90%, or 100% of atrial events are paced atrial events for one minute, several minutes, one hour, several hours, one day, several days, or other selected time period, control circuit 80 may switch to the power saving state at block 308.

In some cases, sustained or intermittent atrial pacing may be delivered due to sustained or intermittent P-wave undersensing. Control circuit 80 may identify episodes of 100% atrial pacing alternating with episodes of 100% sensing of low amplitude P-waves. Processing of atrial signals during intermittent pacing due to P-wave undersensing may drain current from power source 98 without being able to detect AT/AF reliably due to undersensing. In this case, switching to the power saving state is warranted. At block 310, if control circuit 80 identifies sustained atrial pacing without atrial sensed events, intermittent atrial pacing interrupted by episodes of low amplitude P-waves suggesting atrial undersensing, or other criteria based on atrial pacing and/or sensing frequency is detected or satisfied, control circuit 80 may switch to the power saving state at block 308.

Other criteria may be applied by control circuit 80 to detect conditions during which AT/AF detection is moot or of limited diagnostic value such that control circuit 80 may switch from the normal state for detecting AT/AF to the power saving state. For example, executing AT/AF detection instructions by processor 92 during certain pacing modes may have limited utility or be irrelevant. One example is an AOO pacing mode during which atrial pacing is being delivered without atrial sensing, which could be a programmable pacing mode of the intracardiac pacemaker of FIG. 2, for example. An IMB performing the techniques disclosed herein may switch to a temporary AOO pacing mode during certain tests or device diagnostic functions, such as impedance measurements or battery tests. AT/AF detection may be temporarily suspended by control circuit 80 during a temporary AOO pacing mode. Control circuit 80 may return to the power saving state (or normal state) to continue any AT/AF detection processing after the device tests are completed and the temporary AOO pacing mode is terminated.

Figure 6:
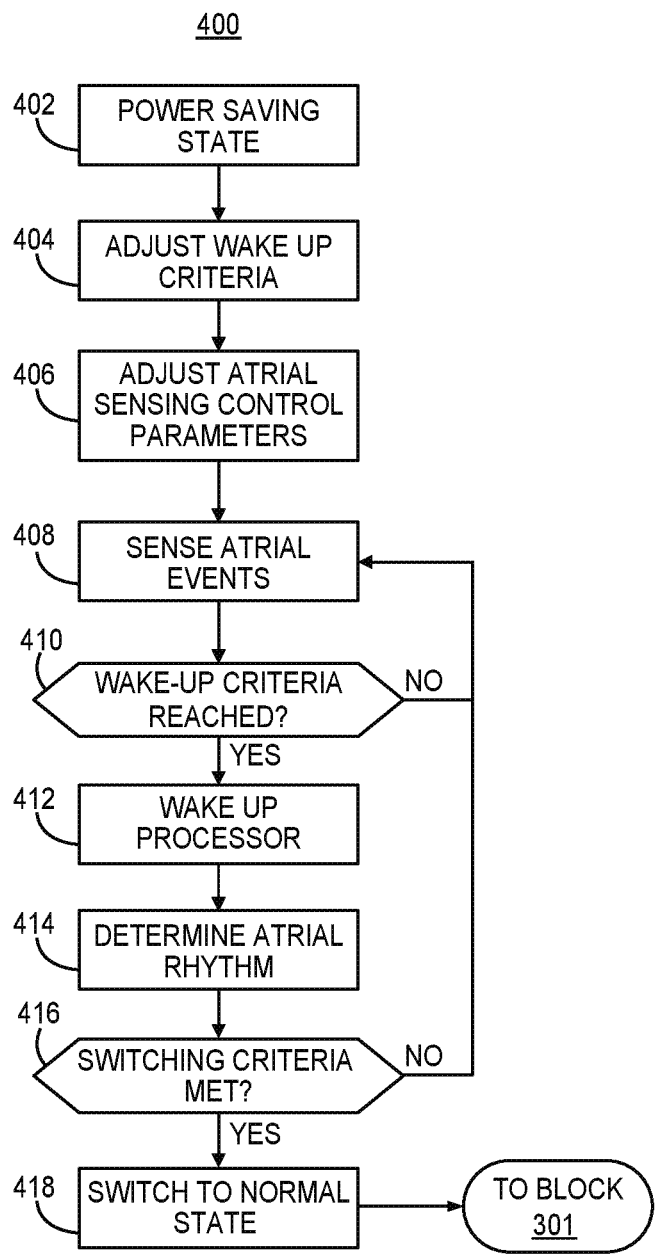
FIG. 6 is a flow chart of operations performed by a medical device during a power saving state of atrial arrhythmia monitoring according to one example.

Other criteria for switching from the normal state to the power saving state may relate to a remaining battery voltage of power source 98 being at or less than a threshold voltage, no change in AT/AF burden over a monitoring period, or no AT/AF detection for a threshold time interval as other examples. IMB 14 may be configured to compute a remaining life of power source 98 based on therapy delivery history, e.g., pacing frequency and shock delivery history, current battery voltage and other factors. When the remaining life of power source 98 reaches a threshold number of weeks or months, or an elective battery replacement indicator (ERI) flag is set, control circuit 80 may switch to the power saving state. It is recognized that numerous criteria for switching to the power saving state may be defined relating to a prolonged or stable state of the atrial rhythm, the current pacing or therapy delivery operating mode of the IMD, and/or the status of power source 98. Once one or more switching criteria are met, control circuit 80 switches to the power saving state at block 308 by advancing to block 402 (FIG. 6). If criteria for switching the atrial arrhythmia detection operating state are unmet, control circuit 80 remains in the normal state and returns to block 301.

FIG. 6 is a flow chart 400 of operations performed by an IMD during the power saving state of atrial arrhythmia monitoring according to one example. At block 402, control circuit 80 enters the power saving state from the normal state. At block 404, control circuit 80 may adjust processor wake up criteria required to be met before waking up processor 92 for processing atrial signal data for AT/AF detection. The wake up criteria are adjusted to decrease the frequency or rate of waking up processor 92 for detecting AT/AF. For instance, control circuit 80 may increase a threshold number of sensed P-waves required for waking up processor 92. In some examples, control circuit 80 includes a counter for counting the number of P-wave sensed event signals received from sensing circuit 86. After switching to the power saving state, control circuit 80 may enable the P-wave sensed event counter to count P-waves sensed by sensing circuit 86 and set a counter threshold value at which processor 92 is woken up for processing atrial signal data for AT/AF detection. During the normal state for monitoring for atrial arrhythmias, processor 92 may be powered up for processing atrial signal data every time a P-wave sensed event signal is received from sensing circuit 86. This rate of processor wake up for data processing that is equal to the rate of sensed P-waves is high when a fast atrial rate is occurring, e.g., during sustained or chronic AT/AF. By reducing the rate at which the processor 92 is woken up for atrial signal processing during the power saving state, current drain of power source 98 is reduced.

As such, at block 404, the value that a P-wave sensed event counter must reach before waking up processor 92 for atrial signal processing, referred to herein as the "wake up count," may be adjusted by control circuit 80. The counter value may be reset to 0 when processor 92 is woken up to process the atrial signal data. The wake up count may be adjusted to be two times, three times, four times, or other multiple of the wake up count required during the normal state. In one example, the processor 92 is woken up after every eight P-wave sensed event signals are received from sensing circuit 86 during the power saving state.

By reducing the rate at which the processor is woken up, the power used for detecting AT/AF can be reduced without disabling AT/AF detection or monitoring of an ongoing AT/AF episode during the power saving state. As such, control circuit 80 may be configured for performing detection of AT/AF, redetection of a sustained episode of AT/AF, detection of a non-AT/AF rhythm, and/or detection of termination of an AT/AF episode during the power saving state. The time of detecting AT/AF or termination of an AT/AF episode may be delayed from the actual onset or ending time of the AT/AF episode depending on the adjusted wake-up count. However, processor 92 may still identify the actual time or cardiac cycle of the onset or termination of the AT/AF episode from the analysis of the atrial signal data.

The adjustment of the wake up count at block 404 may be made independently of processor wake ups scheduled for other signal processing purposes. For example, processor 92 may be woken up for processing ventricular signal data, activity sensor signal data or other sensor signal data at other time intervals or sensed event counts for the purposes of detecting other conditions of the patient, such as detecting ventricular arrhythmias, determining a metric of patient physical activity, or determining patient posture as a few examples. Accordingly, the adjustment to the wake up count at block 404 may be performed to conserve power used for detecting AT/AF without altering the other operations of processor 92 performed for controlling therapy delivery and/or detecting other patient conditions.

In other examples, the wake-up criteria are adjusted at block 404 to reduce the rate of processor wakeups for AT/AF detection by scheduling the wake-up of processor 92 for atrial arrhythmia detection to coincide with another scheduled wake-up of processor 92. For example, if the power saving state is entered due to an AT/AF episode being detected for greater than a threshold duration of time, multiple P-wave sensed event signals may be received between every two consecutive R-wave sensed event signals. Processor 92 may be woken up for detecting ventricular arrhythmias in response to receiving each R-wave sensed event signal from sensing circuit 86. During the power saving state, processor wake ups for AT/AF detection may be scheduled to coincide with processor wake ups triggered by each R-wave sensed event signal. In other examples, atrial signal processing for AT/AF detection may be scheduled to occur when processor 92 is woken up to process signals from activity sensor 96. For instance, processor 92 may be woken up at two second intervals or another predetermined time interval for processing the signal received from activity sensor 96 for determining a metric of patient physical activity. Atrial signal processing may be performed by processor 92 at the scheduled activity sensor signal processing wake up intervals. In this way, AT/AF detection algorithms are piggy-backed on other scheduled processor wake up times instead of waking up the processor solely for detecting AT/AF.

In other examples, processor wake up criteria may be adjusted based on a change in the rate of P-wave sensed event signals counted between processor wake ups. For example, the hardware of sensing circuit 86 and control circuit 80 may be configured to count P-wave sensed event signals over a specified time interval or between R-wave sensed event signals. The count of P-wave sensed event signals over a limited time interval may be used as an indication of atrial rate without requiring wake up of processor 92. The count of P-wave sensed event signals may be compared to a threshold or to a previous count to determine if a change in the indicated atrial rate has occurred. This process of detecting a change in indicated atrial rate based on P-wave sensed event count may be implemented in hardware without requiring wake up of the processor 92. If a change in the atrial rate is indicated based on sensed P-wave counts or PP intervals timed by timing circuit 94, control circuit 80 may wake up processor 92 to process atrial signal data for AT/AF detection. In this way, if the atrial rate indicated by the count of P-wave sensed events or PP intervals determined by timing circuit 94 remains relatively unchanged, processor 92 is not woken up for processing atrial signal data for AT/AF detection. The atrial rhythm may be deemed unchanged (indicating a sustained AT/AF episode or sustained normal sinus rhythm) making repeated execution of the AT/AF detection algorithm by processor 92 unnecessary and a relatively low priority of power usage.

In addition to or alternatively to adjusting the wake up criteria at block 404, control circuit 80 may adjust P-wave sensing control parameters at block 406 to reduce power consumption during the power saving state. For example, the atrial sensing channel 87 may be disabled for intervals of time or predetermined number of ventricular cycles to conserve power. A sense amplifier, ADC, and/or other circuitry included in atrial sensing channel 87 for sensing P-waves and producing an atrial EGM signal passed to control circuit 80 may be powered down then powered up for alternating time periods for example. The time periods may be set to 2 seconds, 5 seconds, 10 seconds, one minute or other time period greater than or less than one minute to reduce power consumed in sensing atrial events. Alternatively, the time periods may be variable and set according to a count of R-wave sensed event signals, for example.

In other examples, the atrial sensing channel 87 may remain enabled but the P-wave sensing threshold may be temporarily increased to intentionally cause P-wave undersensing. In this way, an absence of P-wave sensed event signals will preclude a P-wave triggered wake up of processor 92 for atrial signal processing. The P-wave sensing threshold may be temporarily increased for predetermined or variable intervals of time as described above then returned to the programmed P-wave sensing threshold for another predetermined or variable interval of time to enable P-wave triggered wake ups of processor 92 for atrial signal processing.

The time intervals that the P-wave sensing threshold is increased to intentionally cause P-wave undersensing and the time intervals that the P-wave sensing threshold is not increased to promote reliable P-wave sensing may be equal or different. For instance, the P-wave sensing threshold may be increased by increasing the atrial sensing channel sensitivity setting in millivolts for an n-second interval or for n R-wave sensed event signals. The P-wave sensing threshold may be decreased by decreasing the atrial sensing channel sensitivity setting (in millivolts) for a multiple of (or a fraction of) the n-second interval or n R-wave sensed event signals. The time interval for which the P-wave sensing threshold is set to its normal level for reliably sensing P-waves may depend at least in part on the minimum number of atrial cycles required to satisfy AT/AF detection criteria. For example, if at least 18 out of 24 atrial cycles are required to satisfy interval and/or morphology criteria for detecting AT/AF, the atrial channel sensitivity may be set to the programmed sensitivity until at least 24 P-wave sensed event signals have been received.

Adjustment of atrial sensing control parameters at block 406 may be performed with or without adjusting the processor wake up criteria at block 404. Since adjustment of atrial sensing control parameters may effectively reduce the rate of waking up processor 92 compared to the normal state without adjusting the wake up criteria at block 404, power used in detecting AT/AF will be reduced. Furthermore, power used for sensing P-waves and/or producing an atrial EGM signal by sensing circuit 86 is reduced.

However, adjustment of atrial sensing control parameters may not always be possible depending on other operating modes of the IMD. For example, if CRT or dual chamber pacing is being delivered, P-wave sensing may be required for controlling atrial synchronized ventricular pacing. In other examples, the atrial rate may be determined from PP intervals and used in discriminating supraventricular tachycardia from ventricular tachycardia in ventricular tachycardia detection algorithms performed by control circuit 80. Accordingly, at block 406, control circuit 80 may first determine whether P-wave sensing is required for controlling ventricular pacing or used in other IMD operations such as ventricular rhythm detection and discrimination during the power saving state. When P-wave sensing is used in other detection algorithms or for controlling other IMD operations such as therapy delivery, adjustment to atrial sensing control parameters at block 406 is withheld. Power savings is achieved by adjusting the wake up count or other wake up criteria at block 404 to reduce the rate at which processor 92 is woken up to perform atrial signal processing for AT/AF detection and thereby conserve power.

At block 408, atrial event sensing by sensing circuit 86 is performed according to any adjustments made at block 406. When a wake up count is reached at block 410 processor 92 is woken up at block 412. The wake up count may be based on a counter value of sensed P-waves, sensed R-waves, number of activity count time intervals or other counted events as established at block 404. At block 414, processor 92 analyzes the atrial signal and data extracted therefrom, e.g., PP intervals, P-wave morphology, P-R intervals, R-P intervals and/or other atrial signal related data for determining the atrial rhythm at block 414. The control circuit 80 may include hardware, such as timing circuit 94, that determines cardiac event intervals between consecutively received sensed event signals from sensing circuit 86 so that circular buffers in memory 82 may be populated with event intervals between processor wake ups. Segments of the digital atrial EGM signal received from atrial channel 87 may be buffered in memory 82 between processor wakeups in some examples. A count of the number of sensed atrial events during each ventricular event interval may be buffered for each ventricular cycle. Processor 92 may analyze the populated buffers of cardiac event intervals, P-wave signal segments, sensed event counts, etc. upon being woken up. In this way, data may be accumulated while processor 92 is asleep and available for processing during less frequent wake ups. In other examples, P-wave signals and/or cardiac event intervals may be accumulated upon processor wake up and analyzed as the events are sensed to determine the current AT/AF state.

The processor 92 may be configured to perform an analysis of the atrial signal and data derived therefrom that is a subset of the analysis performed by processor 92 for determining whether AT/AF is present during the power saving state. For example, fewer steps, comparisons or criteria may be applied for detecting AT/AF or for detecting termination of a sustained AT/AF episode that triggered entry into the power saving state. The atrial signal analysis performed by processor 92 upon each wake up may require less power from the power source 98 than the atrial signal analysis performed upon each wake up during the normal state.

A flag indicating the atrial rhythm determined at block 414 may be set in memory 82, e.g., indicating an AT/AF detection or non-AT/AF detection (e.g., normal sinus rhythm). An atrial EGM signal segment may be stored in memory 82 in response to detecting AT/AF. An AT/AF burden may be determined and updated in memory 82 and/or other AT/AF metrics may be updated in memory 82 for providing atrial rhythm information to a clinician upon interrogation of IMD 14. The response to AT/AF detection during the power saving state may be the same response provided during the normal state even though the rate of making AT/AF detections is reduced. In other examples, the response to an AT/AF detection such as storing an EGM signal segment, PP interval or other AT/AF episode data may be performed during the normal state and not performed during the power saving state.

At block 416, control circuit 80 determines if AT/AF detection state switching criteria are met. In some examples, control circuit 80 operates in the power saving state for a fixed time interval. Control circuit 80 may set a timer to a predetermined time interval, e.g., 1 minute, 10 minutes, 30 minutes, one hour, four hours, eight hours, 24 hours or other time interval ranging from several minutes to several hours or even days. Control circuit 80 may switch from the power saving state to the normal state after a fixed interval of time operating in the power saving state. In other examples, control circuit 80 may include a clock to schedule the switch back to the normal saving state at a specified time of day. For instance, AT/AF detection according to the power saving state may be performed during daytime hours, during night time hours, or during various time intervals throughout a 24 hour period. Control circuit 80 may determine that switching criteria are met at block 416 according to a scheduled time of day and switch back to the normal state at block 418.

In other examples, criteria for switching back to the normal state that may be met at block 416 may be the reversal of a condition that caused control circuit 80 to switch from the normal state to the power saving state. In this case, control circuit 80 may set the criteria applied at block 416 for switching from the power saving state to the normal state based on the switching criteria that triggered entrance into the power saving state. Control circuit 80 sets the criteria and monitors the parameters necessary for determining when the switching criteria are met at block 416. For instance, if an AT/AF episode that is sustained for greater than a threshold duration caused control circuit 80 to switch to the power saving state (e.g., at blocks 306 and 308 of FIG. 5) and is determined to be terminated during the power saving state at block 414, control circuit 80 may switch back to the normal state at block 418. In other examples, if the frequency of atrial pacing caused the switch to the power saving state, switching criteria may be met at block 416 when the atrial pacing frequency decreases, resulting in a switch back to the normal state at block 418. In these examples, control circuit 80 may monitor only the parameter, e.g., atrial rate, atrial pacing frequency, or time duration, which caused the switch to the power saving state in order to detect power saving state exit criteria being met at block 416.

In still other examples, a change in pacing mode, a detected ventricular tachyarrhythmia, change in ventricular rate, change in user programmed parameters or other event that warrants more frequent analysis of atrial signal processing for AT/AF detection may satisfy criteria at block 416 for switching back to the normal state at block 418. Control circuit 80 does not necessarily wait until after each processor wake up and atrial rhythm determination during the power saving state to determine if switching criteria are met as generally indicated by the flow of flow chart 400. It is to be understood that any time switching criteria become satisfied during the power saving state, which may be between processor wake ups, the control circuit 80 may switch back to the normal state at block 418. Control circuit 80 returns to the normal state by advancing to block 301 of FIG. 5.

Figure 7:
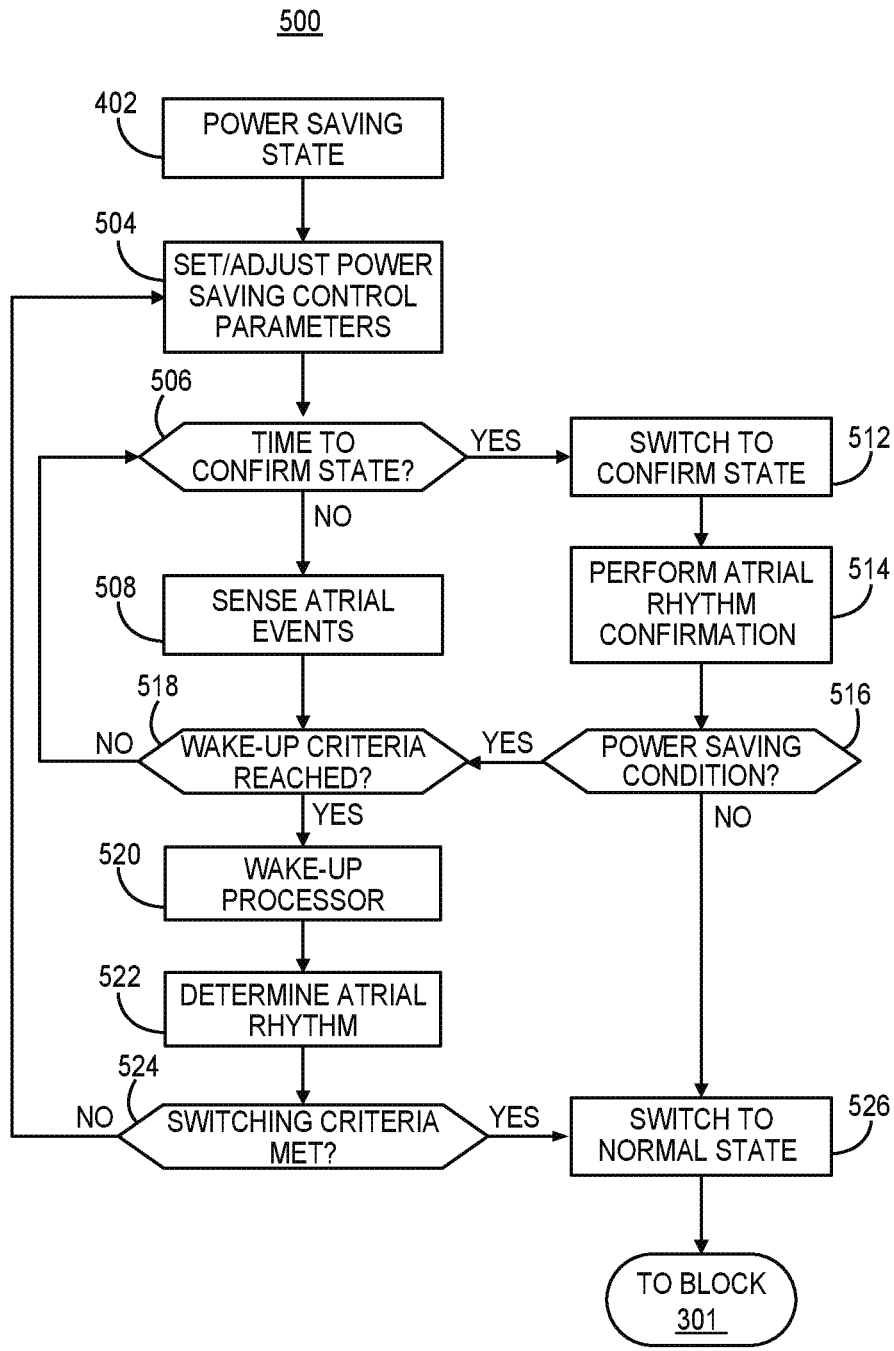
FIG. 7 is a flow chart of a method for controlling the operating state of AT/AF monitoring and detection by a medical device according to another example.

FIG. 7 is a flow chart 500 of a method for controlling the operating state of cardiac arrhythmia monitoring and detection, e.g., AT/AF monitoring and detection, by an IMB according to another example. Control circuit 80 enters the power saving state for AT/AF monitoring and detection at block 402, e.g., from block 308 of FIG. 5. At block 504, control parameters used for sensing atrial signals and/or waking up processor 92 for processing atrial signals are adjusted according to the power saving state, e.g., according to any of the examples described above. During the power saving state, control circuit 80 may determine when it is time to switch to a confirm state at block 506 to confirm that the power saving state is still the appropriate state to operate in.

Criteria applied at block 506 for determining whether to switch to the confirm state at block 512 may include a scheduled duration of time in the power saving state, a detected change in ventricular rhythm (e.g., change in intrinsic ventricular rate, intrinsic ventricular rate stability, or ventricular tachyarrhythmia detection), a change in atrial pacing frequency, or a change in patient activity or posture. In some examples, factors or conditions that may trigger a switch to the confirm state at block 506 may be conditions that can be detected by hardware functions of control circuit 80. For example, hardware included in sensing circuit 86 and control circuit 80 may determine a P-wave sensed event count during a ventricular cycle or other predetermined time interval and detect a change in the number of P-waves counted indicating a possible change in atrial rate, meeting criteria for switching to the confirm state. In other examples, hardware included in control circuit 80 and therapy delivery circuit 84 may determine a change in ventricular or atrial pacing frequency. In other examples, criteria for switching to the confirm state may be determined by processor functions that are performed when the processor 92 is woken up for ventricular rhythm analysis, patient activity analysis or other processing functions that do not include atrial signal analysis for AT/AF detection.

As long as confirm state criteria are not satisfied at block 506, atrial events are sensed according to the power saving state at block 508. When the processor wake up criteria are satisfied at block 518, e.g., based on a P-wave sensed event count reaching a threshold value, processor 92 is powered up at block 520 to perform atrial signal analysis to determine the atrial rhythm at block 522, e.g., detect AT/AF when detection criteria are satisfied. At block 524, control circuit 80 may determine that switching criteria are satisfied for switching directly to the normal state at block 526. Criteria applied at block 524 for switching directly back to the normal state may correspond to any of the examples described above in conjunction with FIG. 6.

If switching criteria are unmet at block 524, control circuit 80 remains in the power saving state by returning to block 504. In this example, control circuit 80 may adjust the power saving state control parameters at block 504 after being in the power saving state for an interval of time. Adjustments to the power saving state control parameters may be made depending on the atrial rhythm determination made at block 522 and/or the duration of time that control circuit 80 has been operating in the power saving state. For example, if the atrial rhythm determined at block 522 has not changed since entering the power saving state, the rate of waking up the processor 92 for processing the atrial signal for AT/AF detection may be reduced. To illustrate, if the power saving state was entered at block 402 due to AT/AF being detected for a sustained threshold duration of time, the rate of waking up processor 92 may initially be set to every eighth sensed P-wave upon entering the power saving state (compared to every sensed P-wave during the normal state). If the AT/AF episode continues to be detected during the power saving state, the wake up count may be increased further at block 504. For instance, if the AT/AF episode has been redetected a threshold number of times, e.g., each time processor 92 has been woken up for n consecutive times, control circuit 80 may increase the wake up count incrementally or by a multiple at block 504. For example, the wake up count may be doubled from a P-wave sensed event count of 8 to a P-wave sensed event count of 16. The wake up count may continue to be increased with increasing duration of operation in the power saving state and no detected change in the AT/AF rhythm.

In other examples, other control parameters may be adjusted at block 504 to decrease the rate or frequency of processor wake ups for AT/AF detection, including wake up criteria and/or atrial sensing control parameters. For example, time intervals of decreased sensitivity of atrial sensing channel 87 may be increased to further reduce the rate or frequency of processor wake ups. In this way, the battery current conserved during the power saving state may be incrementally increased with each adjustment of the power saving state control parameters made at block 504.

At any time that the criteria for switching to the confirm state are satisfied at block 506, control circuit 512 switches to the confirm state at block 512. The confirm state may differ from the normal state in that the criteria for switching back to the power saving state may be different. For example, when control circuit 80 switches from the power saving state to the normal state, any timers or counters used to monitor switching criteria may be reset. As such, upon switching from the power saving state or confirm state to the normal state, a timer used to track the duration of a sustained AT/AF episode may be reset to zero. The threshold duration of an AT/AF episode is required to be reached again before switching back to the power saving state. However, in the confirm state, an atrial signal analysis at block 514 that results in determining no change in the atrial rhythm ("yes" branch of block 516) results in direct return to the power saving state. Return to the power saving state may resume where it left off in reaching processor wake up criteria at block 518 according to the currently set power saving state control parameters. For example, a P-wave sensed event counter may not be reset upon switching to the confirm state and back into the power saving state.

In other examples, control circuit 80 may switch from the confirm state back to the power saving state with any P-wave sensed event counter or other counters, timers or criteria monitored for scheduling the next processor wake-up at block 520 reset to a starting point. In still other examples, control circuit 80 may determine an atrial rate at block 514 during the confirm state and if the atrial rate has changed, control circuit 80 may return to the power saving state directly to block 520 for waking up processor 92 to perform the full AT/AF detection algorithm for determining the atrial rhythm. A determination as to whether switching criteria are met for switching to the normal state at block 524 may then be made based on the results of the AT/AF detection algorithm determined at block 522.

Steps or processes performed to confirm the atrial rhythm at block 514 may include a full atrial signal analysis, e.g., interval and/or morphology analysis, as performed by processor 92 at block 522. In other examples, different criteria and/or fewer comparisons, fewer atrial cycles or sensed P-waves, or other parameters or functions performed may be downgraded or reduced during the confirm state to enable a relatively quick verification of the atrial rhythm for confirmation that remaining in the power saving state continues to be appropriate. Limited processing of the atrial signal and/or a subset of AT/AF detection algorithm steps may be performed to confirm an unchanged atrial rhythm or detect a changed atrial rhythm. For example, an atrial rate may be determined at block 514 based on a limited, predetermined number of P-wave sensed event intervals to verify that the atrial rate has not changed from a previously detected atrial rate during an AT/AF rhythm.

One or more conditions may be determined during the confirm state at block 514 to determine if a direct return to the power saving state is appropriate or if a switch to the normal state is warranted. For example, control circuit 80 may verify that the atrial rhythm is unchanged based on PP intervals, no P-wave sensed events received for a threshold time interval or that the pacing mode or other IMD operating modes renders determination of the atrial rhythm moot. One of these conditions may justify remaining in the power saving state ("no branch" of block 516). As such, even if the atrial rhythm or rate changes, another condition that justifies remaining in the power saving state may be satisfied at block 516.

Control circuit 80 may additionally check conditions or criteria at blocks 514 and 516 that warrant a switch to the normal state. For example, in addition to checking for criteria such as no change in atrial rate corresponding to a power saving state condition at block 516, control circuit 80 may check for one or more normal state conditions at block 516. Such conditions may include a change in the ventricular rhythm or a change in pacing mode or other operating state that requires normal atrial P-wave sensing for proper system operation. If one or more normal state conditions are satisfied at block 516, control circuit 80 may switch from the confirm state directly to the normal state at block 526. Normal state AT/AF monitoring and detection operations are resumed by advancing to block 301 of FIG. 5.

As such, in some examples, a confirm state is entered only from the power saving state but may transition to either the power saving or normal state, depending upon confirmation of one or more conditions that warrant remaining in the power saving state. If such conditions are not confirmed, control circuit 80 may switch to the normal state. The confirm state may differ from the power saving state in that conditions other than the atrial rhythm status may be checked for verifying the appropriateness of remaining in the power saving state.

Operation in the power saving state reduces current drain associated with AT/AF monitoring and detection that may translate to an extension of the useful life of the IMD from weeks to months or even years. For example, in some patients experiencing relatively high AT/AF burden or chronic AT/AF, current due to atrial signal processing and atrial EGM storage in IMD memory 82 may reduce the useful life of the IMD by several months or even up to two years or more in some instances. Accordingly, the overall IMD performance in providing chronic rhythm monitoring and therapy delivery is improved by extension of the useful life of the IMD power supply through selective switching between the normal and power saving states while still providing AT/AF detection capabilities during the power saving state.

Figure 8:
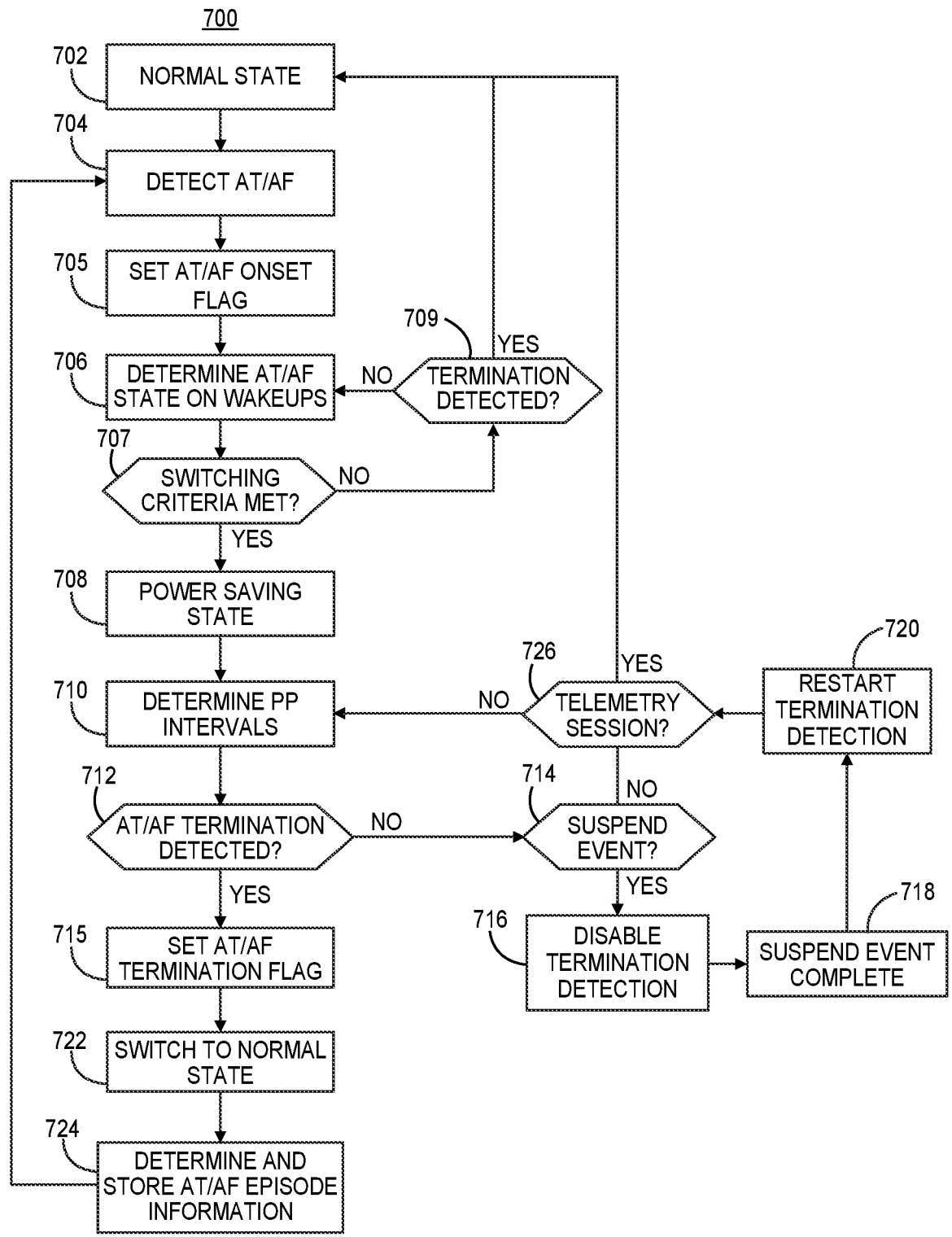
FIG. 8 is a flow chart of a method for controlling atrial arrhythmia detection state by a medical device according to another example.

FIG. 8 is a flow chart 700 of a method for controlling atrial arrhythmia detection state by an IMD according to another example. At block 702, control circuit 80 is operating in the normal state, during which the processor 92 is analyzing the atrial signal and data derived therefrom according to a normal state processor wake up schedule and normal atrial event sensing control parameters. In one example, the processor 92 is woken upon every $8^{th}$ P-wave sensed from a cardiac electrical signal received by sensing circuit 86 to determine an atrial arrhythmia state. In some examples, hardware of control circuit 80, including timing circuit 94, is configured to detect AT/AF. Each P-wave sensed event signal may cause a PP interval to time out by timing circuit 94 and buffered in memory 82 in a circulating buffer that stores the required number of PP intervals needed for detecting AT/AF. In other examples, timing circuit 94 times out RR intervals (which may be paced or sensed RR intervals) and a counter included in control circuit 80 counts the number of P-waves sensed by sensing circuit 86 during each RR interval. P-wave counts for a predetermined number of RR intervals may be buffered in memory 82 for use in detecting AT/AF. P-wave signal segments may additionally be stored in memory 82 to enable waveform morphology analysis or determination of other P-wave features for use in detecting AT/AF. The P-wave sensed event data may be stored in a circulating buffer and analyzed by processor 92 in response to being woken up upon every nth P-wave sensed event signal, according to a normal state processor wake up count.

At block 704, the control circuit 80 detects AT/AF. In some examples, AT/AF is detected based on an analysis performed by the processor 92. In other examples, hardware included in control circuit 80 and sensing circuit 86 may be configured to detect AT/AF without waking up processor 92. For example, AT/AF may be detected at block 706 based on a required number of PP intervals being less than an AT/AF detection interval or a required number of consecutive RR intervals including multiple sensed P-waves. In one example, AT/AF onset is detected in response to 18 out of 24 PP interval being less than or equal to an AT/AF detection interval of 350 ms or less, as an example. The AT/AF detection interval may correspond to an atrial rate that is greater than 180 beats per minute (e.g., 333 millisecond PP interval) and may be programmed according to individual patient need.

At block 705, control circuit 80 may set an AT/AF onset flag in response to detecting AT/AF, e.g., in response to hardware-based detection criteria being satisfied such as N of M PP intervals being equal to or less than an AT/AF detection interval. In response to the AT/AF onset flag being set, control circuit 80 may switch to the power saving state at block 708, during which the rate of waking up processor 92 is reduced compared to the normal state. In some examples, however, control circuit 80 may remain in the normal state after setting the AT/AF onset flag until power saving state switching criteria are met at block 707.

For instance, the detected AT/AF episode may be required to be sustained for a threshold interval of time, which may be any of the threshold duration examples given above, before switching to the power saving state. In the meantime, after setting the AT/AF flag, the processor 92 may be woken up according to the normal state wake up count at block 706 to determine a state of the detected AT/AF episode. For example, processor 92 may be woken up on every $8^{th}$ P-wave sensed event signal received from sensing circuit 86 to determine an updated AT/AF episode duration to determine if switching criteria are met at block 707. In one example, the AT/AF episode is required to be sustained for at least six minutes before switching to the power saving state at block 708. Until the switching criteria are met, processor 92 may be woken up to process event intervals, signal waveforms, and/or other episode data, which may include historical AT/AF episode data, to determine an atrial arrhythmia state. Determination of the atrial arrhythmia state may include one or more of detecting the atrial arrhythmia, detecting termination of the atrial arrhythmia, determining the duration of a detected AT/AF episode, determining the rate of the AT/AF episode, determining an updated AT/AF burden or determining other detected AT/AF episode information that requires execution of firmware or software by processor 92.

In some cases, termination of the AT/AF episode may be detected at block 709 prior to switching criteria being met at block 707. AT/AF episode termination may be detected by control circuit 80 according to hardware implemented criteria, e.g., P out of Q consecutive PP intervals being greater than the AT/AF detection interval. In other examples, AT/AF termination may be detected by processor 92 based on analysis of atrial signals upon wake up. If termination is detected, the control circuit 80 remains in the normal state and returns to block 702 to await the next AT/AF detection. If termination is not detected, processor 92 continues to be woken up according to the normal state wake up count to update a state of the detected AT/AF episode, e.g., the episode duration, until the switching criteria are met at block 708. Processor 92 may store an EGM signal representative of the AT/AF episode When the AT/AF episode reaches a threshold duration, for example, control circuit 80 switches to the power saving state at block 708.

During the power saving state, control circuit 80 may reduce the rate of waking up processor 92 by withholding processor wakeups during the power saving state. Control circuit 80 may withhold processor wake ups until AT/AF termination is detected. Termination of AT/AF may be detected by detecting a threshold number of sensed atrial events occurring at a rate that is slower than an atrial arrhythmia detection rate. In some examples, processor 92 may be woken up by control circuit 80 for performing other required device functions, however processor 92 is not woken up during the power saving state for determining a state of the detected atrial arrhythmia. Control circuit 80 may withhold processor wakeups by disabling a counter included in control circuit 80 that counts the number of P-wave sensed events up to the wake up count.

Control circuit 80 may continue to count P-waves and determine PP intervals by timing circuit 94 at block 710 for detecting termination of the sustained AT/AF episode during the power saving state based on hardware implemented termination detection criteria. Termination of AT/AF may be detected by detecting a threshold number of sensed atrial events occurring at a rate that is slower than an atrial arrhythmia detection rate. Control circuit 80 may count PP intervals that are greater than the atrial arrhythmia detection interval. When P out of Q consecutive PP intervals are greater than the atrial arrhythmia detection interval, AT/AF termination is detected at block 712. In one example, AT/AF termination is detected in response to at least 10 out of 20 PP intervals being greater than the AT/AF detection interval, e.g., 330 to 350 ms. In another example, a threshold number of sensed atrial events occurring at a rate that is slower than the AT/AF detection rate may be detected based on a single P-wave being sensed during each RR interval of a predetermined number of RR intervals. In these examples, the wake up criteria adjusted to reduce the rate of processor wakes ups may be defined as the detection of AT/AF termination. Processor wake ups may be withheld from the time of switching criteria being met at block 707 until AT/AF termination is detected by control circuit 80 based on sensed atrial event signals monitored by hardware included in control circuit 80.

Upon AT/AF termination detection, control circuit 80 may set an AT/AF termination flag at block 715. Control circuit 80 switches to the normal state at block 722 in response to the termination flag being set. At block 724, the processor 92 is woken up at the next wake up count in response to the control circuit 80 switching back to the normal state. At block 724, processor 92 may update AT/AF episode information at block 724. For example, processor 92 may determine the total episode duration based on the time that the onset flag was set and the time that the termination flag was set. Processor 92 may determine other AT/AF episode information such as an updated AT/AF burden. An updated state of the AT/AF episode may be stored in memory 82.

In some examples, upon being woken up, processor 92 may analyze PP intervals and/or P-wave signal segments for verifying AT/AF termination. In other examples, control circuit 80 may wake up processor 92 upon setting the AT/AF flag, before switching back to the normal state. Processor 92 may analyze atrial signals for detecting termination of the AT/AF episode to confirm the hardware based detection. If termination is not confirmed by the analysis performed by processor 92 after the AT/AF offset detection flag is set, control circuit 80 may remain in the power saving state. Control circuit 80 may wake up processor 92 again the next time AT/AF termination detection criteria are met, which may include resetting all PP interval counters to start again from zero in counting the P out of Q consecutive PP intervals greater than the AT/AF detection interval.

It is recognized that the medical may perform device diagnostics or other testing during the power saving state or the device may enter a telemetry session with another medical device, e.g., when a user interrogates the IMB using external device 50 (FIG. 1). In these situations, a temporary pacing mode and/or acquisition and transmission of an EGM signal may be performed. Such actions may require a suspension or termination of the power saving state. Determination of PP intervals for detecting the AT/AF termination may be precluded, e.g., if a temporary AOO pacing mode is enabled for performing impedance measurements or other tests. If AT/AF termination has not yet been detected at block 712 during the power saving state, control circuit 80 may determine if a suspend event is detected at block 714. The suspend event may include switching to an AOO pacing mode or other device diagnostic testing, impedance measurements, or the like which may interfere with counting PP intervals toward detecting termination criteria. When a suspend event is detected, control circuit 80 disables termination detection at block 716 and waits for the suspend event to be completed at block 718. For example, the suspend event is completed when a temporary AOO pacing mode is terminated or a device test or measurement is completed.

When the suspend event is complete, control circuit 80 restarts AT/AF termination detection, e.g., by re-starting counting of PP intervals that are greater than the AT/AF detection interval. The PP interval counters may be reset when the suspend event is detected so that termination detection is restarted at block 720 instead of being resumed from an existing count of PP intervals at the time that the suspend event was detected. In other examples, the AT/AF termination detection may be resumed from the existing state, e.g., the existing PP interval counter values, at the time that the suspend event was detected. In this way, during the power saving state, AT/AF termination detection may be suspended, particular when such a determination may be confounded by temporary medical device operations.

At block 726, control circuit 80 may detect a telemetry session that has been entered into by telemetry circuit 88. Telemetry circuit 88 may enter a telemetry session when a user transmits an interrogation request, e.g., using external device 50 (FIG. 1), which may happen to occur when the power saving state is in effect. Another medical device such as a home monitor or patient hand held device may request data from the medical device performing the process of flow chart 700 according to a regularly scheduled interrogation session. When the regularly scheduled interrogation session happens to fall during the power saving state, control circuit 80 may detect the telemetry session at block 726. In still other examples, telemetry circuit 88 may initiate a telemetry session with another device according to a regularly scheduled data transmission time or in response to a triggering event.

In response to determining that telemetry circuit 88 is communicating with (or about to communicate with) another device, control circuit 80 switches from the power saving state to the normal state by advancing to block 702. During the normal state, processor 92 is enabled to be woken up according to wake up criteria for processing data and EGM signals produced by sensing circuit 86, which are then available for transmission by telemetry circuit 88. Control circuit 80 may withhold switching back to the power saving state until the telemetry session is complete and any other power saving state switching criteria are again satisfied.

If the AT/AF episode that was detected prior to switching to the power saving state is still sustained upon switching back to the normal state at block 702, in response to detecting a telemetry session at block 726, it is recognized that the sustained AT/AF episode is not detected as a new episode at block 704. The AT/AF onset flag previously set upon detecting the sustained AT/AF episode is not set again at block 705 upon re-entering the normal state. Blocks 704 and 706 may be skipped upon re-entering the normal state in response to detecting a telemetry session at block 726. Control circuit 80 may wake up processor 92 to determine the state of the sustained AT/AF episode at block 706 according to the normal state processor wake up criteria. Control circuit 80 monitors for termination of the sustained AT/AF episode at block 709. If the telemetry session ends and the AT/AF episode is still sustained, meeting switching criteria at block 707, control circuit 80 may switch back to the power saving state at block 708.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units, circuits or processors associated with, for example, a medical device.

In one or more examples, the functions described may be implemented in hardware, software, firmware, or any combination thereof. If implemented in software or firmware, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

The invention claimed is:

1. A medical device, comprising:
a sensing circuit configured to sense a cardiac signal;
a power source; and
a control circuit comprising a processor powered by the power source, wherein the control circuit is configured to:
  operate in a normal state by waking up the processor at a first rate to analyze the cardiac signal;
  switch from the normal state to a power saving state that uses less electrical power from the power source than the normal state; and
  operate in the power saving state by waking up the processor at a second rate to analyze the cardiac signal, the second rate being less than the first rate.

2. The medical device of claim 1, wherein:
the sensing circuit is configured to sense cardiac event signals attendant to myocardial depolarizations from the cardiac signal;
the control circuit is further configured to:
  wake up the processor at the first rate during the normal state by waking up the processor each time a first predetermined number of the cardiac event signals are sensed by the sensing circuit; and
  wake up the processor at the second rate during the power saving state by waking up the processor each time a second predetermined number of the cardiac event signals are sensed by the sensing circuit, the second predetermined number of cardiac event signals being greater than the first predetermined number of cardiac event signals.

3. The medical device of claim 1, wherein the control circuit is further configured to:
operate in the normal state by waking up the processor at the first rate to analyze the cardiac signal for detecting an arrhythmia; and
operate in the power saving state by waking up the processor at a second rate to analyze the cardiac signal for determining if the arrhythmia is present, the second rate being less than the first rate.

4. The medical device of claim 3, wherein the processor is configured to:
perform a first analysis of the cardiac signal for detecting the arrhythmia during the normal state; and
perform a second analysis of the cardiac signal for determining if the detected arrythmia is present during the power saving state, wherein the second analysis requires less power from the power source than the first analysis.

5. The medical device of claim 3, wherein the control circuit is configured to:
detect the arrhythmia in the normal state;
determine that the detected arrhythmia is sustained for a predetermined period of time;
switch from the normal state to the power saving state in response to determining that the detected arrhythmia is sustained for the predetermined period of time;
determine that the arrhythmia is not present during the power saving state; and
switch from the power saving state to the normal state in response to determining that the arrhythmia is not present.

6. The medical device of claim 1, further comprising a memory, wherein the control circuit is configured to:
buffer in the memory cardiac signal data between processor wake ups;
wake up the processor at the first rate to analyze the cardiac signal data buffered in the memory between the processor wake ups at the first rate; and
wake up the processor at the second rate to analyze the cardiac signal data buffered in the memory between the processor wake ups at the second rate.

7. The medical device of claim 6, wherein:
the sensing circuit is configured to sense cardiac event signals attendant to myocardial depolarizations from the cardiac signal; and
the control circuit is configured to:
  determine cardiac event intervals based on the cardiac event signals sensed by the sensing circuit; and
  buffer the cardiac signal data between the processor wake ups by buffering the cardiac event intervals.

8. The medical device of claim 6, wherein the control circuit is configured to buffer the cardiac signal data between the processor wake ups by buffering at least one segment of the cardiac signal in the memory.

9. The medical device of claim 1, further comprising:
a therapy delivery circuit;
a housing enclosing the therapy delivery circuit, the sensing circuit and the control circuit; and
a plurality of electrodes carried by the housing;
wherein:
the sensing circuit is configured to:
  receive the cardiac signal from a first electrode pair of the plurality of electrodes carried by the housing; and
  sense atrial event signals from the cardiac signal; and
the therapy delivery circuit is configured to generate ventricular pacing pulses synchronized to the atrial event signals sensed from the cardiac signal.

10. The medical device of claim 9, wherein the therapy delivery circuit is coupled to a second electrode pair of the plurality of electrodes carried by the housing for delivering the atrial synchronized ventricular pacing pulses.

11. The medical device of claim 9 wherein the plurality of electrodes comprises a tip electrode configured to be positioned for delivering ventricular pacing pulses to the native ventricular conduction system.

12. A method, comprising:
sensing a cardiac signal;
operating in a normal state by waking up a processor at a first rate to analyze a cardiac signal;
switching from the normal state to a power saving state that uses less electrical power from a power source than the normal state; and
operating in the power saving state by waking up the processor at a second rate to analyze the cardiac signal, the second rate being less than the first rate.

13. The method of claim 12, further comprising:
sensing cardiac event signals attendant to myocardial depolarizations from the cardiac signal;
waking up the processor at the first rate during the normal state by waking up the processor each time a first predetermined number of the cardiac event signals are sensed; and
waking up the processor at the second rate during the power saving state by waking up the processor each time a second predetermined number of the cardiac event signals are sensed, the second predetermined number of cardiac event signals being greater than the first predetermined number of cardiac event signals.

14. The method of claim 12, further comprising:
operating in the normal state by waking up the processor at the first rate to analyze the cardiac signal for detecting an arrhythmia; and
operating in the power saving state by waking up the processor at a second rate to analyze the cardiac signal for determining if the arrhythmia is present, the second rate being less than the first rate.

15. The method of claim 14, further comprising:
performing a first analysis of the cardiac signal for detecting the arrhythmia during the normal state; and
performing a second analysis of the cardiac signal for determining if the detected arrythmia is present during the power saving state, wherein the second analysis requires less power from the power source than the first analysis.

16. The method of claim 14, further comprising:
detecting the arrhythmia in the normal state;
determining that the detected arrhythmia is sustained for a predetermined period of time;
switching from the normal state to the power saving state in response to determining that the detected arrhythmia is sustained for the predetermined period of time;
determining that the arrhythmia is not present during the power saving state; and
switching from the power saving state to the normal state in response to determining that the arrhythmia is not present.

17. The method of claim 12, further comprising:
buffering in a memory cardiac signal data between processor wake ups;
waking up the processor at the first rate to analyze the cardiac signal data buffered in the memory between the processor wake ups at the first rate; and
waking up the processor at the second rate to analyze the cardiac signal data buffered in the memory between the processor wake ups at the second rate.

18. The method of claim 17, further comprising:
sensing cardiac event signals attendant to myocardial depolarizations from the cardiac signal;
determining cardiac event intervals based on the cardiac event signals sensed by the sensing circuit; and
buffering the cardiac signal data between the processor wake ups by buffering the cardiac event intervals.

19. The method of claim 17, wherein buffering the cardiac signal data between the processor wake ups comprises buffering at least one segment of the cardiac signal in the memory.

20. The method of claim 12, further comprising:
receiving the cardiac signal from a first electrode pair of a plurality of electrodes carried by a housing;
sensing atrial event signals from the cardiac signal; and
generating ventricular pacing pulses synchronized to the atrial event signals sensed from the cardiac signal.

21. The method of claim 20, further comprising delivering the atrial synchronized ventricular pacing pulses via a second electrode pair of the plurality of electrodes carried by the housing.

22. A non-transitory, computer-readable storage medium comprising a set of instructions which, when executed by a control circuit of a medical device, causes the medical device to:
sense a cardiac signal;
operate in a normal state by waking up a processor of the control circuit at a first rate to analyze a cardiac signal;
switch from the normal state to a power saving state that uses less electrical power from a power source of the medical device than the normal state; and
operate in the power saving state by waking up the processor at a second rate to analyze the cardiac signal, the second rate being less than the first rate.

* * * * *